(12) United States Patent
Dücker et al.

(10) Patent No.: US 6,958,152 B2
(45) Date of Patent: Oct. 25, 2005

(54) HUMAN PHOSPHOLIPASE C DELTA 5

(75) Inventors: Klaus Dücker, Darmstadt (DE); Silke Brandt, Darmstadt (DE); Johannes Gleitz, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 451 days.

(21) Appl. No.: 10/258,860

(22) PCT Filed: Apr. 27, 2001

(86) PCT No.: PCT/EP01/04784

§ 371 (c)(1),
(2), (4) Date: Oct. 29, 2002

(87) PCT Pub. No.: WO01/83771

PCT Pub. Date: Nov. 8, 2001

(65) Prior Publication Data

US 2003/0100039 A1 May 29, 2003

(30) Foreign Application Priority Data

Apr. 29, 2000 (EP) .......................... 00109318

(51) Int. Cl.$^7$ .......................... A61K 39/00; C12N 9/22; C12N 1/20; C12N 15/00; C07H 21/04
(52) U.S. Cl. ................. 424/192.1; 435/198; 435/252.3; 435/320.1; 536/23.2
(58) Field of Search ....................... 424/192.1; 435/198, 435/252.3, 320.1; 536/23.2

(56) References Cited

FOREIGN PATENT DOCUMENTS

EP          0731164 A      9/1996

OTHER PUBLICATIONS

Lee, et al.: "Molecular cloning, splice variants, expression and purification of phospholipase C–delta4", The Journal of Biological Chemistry, vol. 271, No. 1, Jan. 5, 1996, pp. 25–31. XP002180350 cited in the application abstract; figure 1.

–&, Database EM_RO 'Online! EMBL; Nov. 17, 1994 Lee, et. al.: "*Rattus norvegicus* phospholipase C delta–4 MRNA, complete cds." Retrieved from EBI, accession No. RN16655 Database accession No. U16655 XP002180352 the whole document.

Liu, et al.: "A new phosphlipase C delta4 is induced at S–phase of the cell cycle and appears in the nucleus" The Journal of Biological Chemistry, vol. 271, No. 1, Jan. 5, 1996, pp. 355–380 CP002180351 abstract, figure 1.

Database EM_EST Online! EMBL; Jan. 11, 1997 Hillier, et al.: "WashU–NCI human EST project" retrieved from EBI, accession No. Al366170 Database accession No. Al366170 XP002180353 the whole document.

Database EM_EST Online! EMBL; Jan. 14, 1997 Hillier, et. al.: "The WashU–Merck EST project" retrieved from EBI, accession No. HSAA41263 Database accession No. AA047627 XP002180354 the whole document.

Database EM_HUM Online! EMBL; Apr. 16, 2001 Strausberg, R: "*Homo sapiens*, clone MGC:12837 Image: 4124286, mRNA, complete cds." Retrieved from EBI accession No. BC006355 Database accession No. BC006355 XP002180355 the whole document.

*Primary Examiner*—Tekchand Saidha
(74) *Attorney, Agent, or Firm*—Millen, White, Zelano & Branigan, P.C.

(57) ABSTRACT

Phospholipase C delta 5 (PLCD5) polypeptides and polynucleotides an methods for producing such polypeptides by recombinant techniques are disclosed. Also disclosed are methods for utilizing phospholipase C delta 5 (PLCD5) polypeptides and polynucleotides in diagnostic assays.

4 Claims, 1 Drawing Sheet

SEQUENCE LISTING

```
<160> NUMBER OF SEQ ID NOS: 12

<210> SEQ ID NO 1
<211> LENGTH: 2289
<212> TYPE: DNA
<213> ORGANISM: Artificial Sequence
<220> FEATURE:
<221> NAME/KEY: CDS
<222> LOCATION: (1)..(2289)
<220> FEATURE:
<223> OTHER INFORMATION: Description of Artificial Sequence: Primer 1

<400> SEQUENCE: 1 atg gcg tcc ctg ctg caa gac cag ctg acc act gat cag gac ttg ctg      48
Met Ala Ser Leu Leu Gln Asp Gln Leu Thr Thr Asp Gln Asp Leu Leu
  1               5                  10                  15 ctg atg cag gaa ggc atg ccg atg cgc aag gtg agg tcc aaa agc tgg      96
Leu Met Gln Glu Gly Met Pro Met Arg Lys Val Arg Ser Lys Ser Trp
             20                  25                  30 aag aag cta aga tac ttc aga ctt cag aat gac ggc atg aca gtc tgg     144
Lys Lys Leu Arg Tyr Phe Arg Leu Gln Asn Asp Gly Met Thr Val Trp
         35                  40                  45 cat gca cgg cag gcc agg ggc agt gcc aag ccc agc ttc tca atc tct     192
His Ala Arg Gln Ala Arg Gly Ser Ala Lys Pro Ser Phe Ser Ile Ser
     50                  55                  60
```

-continued

| | | |
|---|---|---|
| gat gtg gag aca ata cgt aat ggc cat gat tcc gag ttg ctg cgt agc<br>Asp Val Glu Thr Ile Arg Asn Gly His Asp Ser Glu Leu Leu Arg Ser<br>65                    70                   75                  80 | 240 |
| ctg gca gag gag ctc ccc ctg gag cag ggc ttc acc att gtc ttc cat<br>Leu Ala Glu Glu Leu Pro Leu Glu Gln Gly Phe Thr Ile Val Phe His<br>               85                   90                   95 | 288 |
| ggc cgc cgc tcc aac ctg gac ctg atg gcc aac agt gtt gag gag gcc<br>Gly Arg Arg Ser Asn Leu Asp Leu Met Ala Asn Ser Val Glu Glu Ala<br>            100                  105               110 | 336 |
| cag ata tgg atg cga ggg ctc cag ctg ttg gtg gat ctt gtc acc agc<br>Gln Ile Trp Met Arg Gly Leu Gln Leu Leu Val Asp Leu Val Thr Ser<br>         115                 120               125 | 384 |
| atg gac cat cag gag cgc ctg gac caa tgg ctg agc gat tgg ttt caa<br>Met Asp His Gln Glu Arg Leu Asp Gln Trp Leu Ser Asp Trp Phe Gln<br>130                  135               140 | 432 |
| cgt gga gac aaa aat cag gat ggt aag atg agt ttc caa gaa gtt cag<br>Arg Gly Asp Lys Asn Gln Asp Gly Lys Met Ser Phe Gln Glu Val Gln<br>145                  150               155               160 | 480 |
| cgg tta ttg cac cta atg aat gtg gaa atg gac caa gaa tat gcc ttc<br>Arg Leu Leu His Leu Met Asn Val Glu Met Asp Gln Glu Tyr Ala Phe<br>                 165               170               175 | 528 |
| agt ctt ttt cag gca gca gac acg tcc cag tct gga acc ctg gaa gga<br>Ser Leu Phe Gln Ala Ala Asp Thr Ser Gln Ser Gly Thr Leu Glu Gly<br>         180                 185               190 | 576 |
| gaa gaa ttc gta cag ttc tat aag gca ttg act aaa cgt gct gag gtg<br>Glu Glu Phe Val Gln Phe Tyr Lys Ala Leu Thr Lys Arg Ala Glu Val<br>               195               200              205 | 624 |
| cag gaa ctg ttt gaa agt ttt tca gct gat ggg cag aag ctg act ctg<br>Gln Glu Leu Phe Glu Ser Phe Ser Ala Asp Gly Gln Lys Leu Thr Leu<br>210                  215               220 | 672 |
| ctg gaa ttt ttg gat ttc ctc caa gag gag cag aag gag aga gac tgc<br>Leu Glu Phe Leu Asp Phe Leu Gln Glu Glu Gln Lys Glu Arg Asp Cys<br>225                  230               235               240 | 720 |
| acc tct gag ctt gct ctg gaa ctc att gac cgc tat gaa cct tca gac<br>Thr Ser Glu Leu Ala Leu Glu Leu Ile Asp Arg Tyr Glu Pro Ser Asp<br>         245                 250               255 | 768 |
| agt ggc aaa ctg cgg cat gtg ctg agt atg gat ggc ttc ctc agc tac<br>Ser Gly Lys Leu Arg His Val Leu Ser Met Asp Gly Phe Leu Ser Tyr<br>             260               265               270 | 816 |
| ctc tgc tct aag gat gga gac atc ttc aac cca gcc tgc ctc ccc atc<br>Leu Cys Ser Lys Asp Gly Asp Ile Phe Asn Pro Ala Cys Leu Pro Ile<br>         275                 280               285 | 864 |
| tat cag gat atg act caa ccc ctg aac cac tac ttc atc tgc tct tct<br>Tyr Gln Asp Met Thr Gln Pro Leu Asn His Tyr Phe Ile Cys Ser Ser<br>290                  295               300 | 912 |
| cat aac acc tac cta gtg ggg gac cag ctt tgt ggc cag agc agc gtc<br>His Asn Thr Tyr Leu Val Gly Asp Gln Leu Cys Gly Gln Ser Ser Val<br>305                  310               315               320 | 960 |
| gag gga tat ata cgg gcc ctg aag cgg ggg tgc cgc tgc gtg gag gtg<br>Glu Gly Tyr Ile Arg Ala Leu Lys Arg Gly Cys Arg Cys Val Glu Val<br>             325               330               335 | 1008 |
| gat gta tgg gat gga cct agc ggg gaa cct gtc gtt tac cac gga cac<br>Asp Val Trp Asp Gly Pro Ser Gly Glu Pro Val Val Tyr His Gly His<br>             340               345               350 | 1056 |
| acc ctg acc tcc cgc atc ctg ttc aaa gat gtc gtg gcc aca gta gca<br>Thr Leu Thr Ser Arg Ile Leu Phe Lys Asp Val Val Ala Thr Val Ala<br>         355                 360               365 | 1104 |
| cag tat gcc ttc cag aca tca gac tac cca gtc atc ttg tcc ctg gag<br>Gln Tyr Ala Phe Gln Thr Ser Asp Tyr Pro Val Ile Leu Ser Leu Glu<br>370                  375               380 | 1152 |

```
acc cac tgc agc tgg gag cag cag cag acc atg gcc cgt cat ctg act       1200
Thr His Cys Ser Trp Glu Gln Gln Gln Thr Met Ala Arg His Leu Thr
385                 390                 395                 400 gag atc ctg ggg gag cag ctg ctg agc acc acc ttg gat ggg gtg ctg       1248
Glu Ile Leu Gly Glu Gln Leu Leu Ser Thr Thr Leu Asp Gly Val Leu
            405                 410                 415 ccc act cag ctg ccc tcg cct gag gag ctt cgg agg aag atc ctg gtg       1296
Pro Thr Gln Leu Pro Ser Pro Glu Glu Leu Arg Arg Lys Ile Leu Val
420                 425                 430 aag ggg aag aag tta aca ctt gag gaa gac ctg gaa tat gag gaa gag       1344
Lys Gly Lys Lys Leu Thr Leu Glu Glu Asp Leu Glu Tyr Glu Glu Glu
        435                 440                 445 gaa gca gaa cct gag ttg gaa gag tca gaa ttg gcg ctg gag tcc cag       1392
Glu Ala Glu Pro Glu Leu Glu Glu Ser Glu Leu Ala Leu Glu Ser Gln
450                 455                 460 ttt gag act gag cct gag ccc cag gag cag aac ctt cag aat aag gac       1440
Phe Glu Thr Glu Pro Glu Pro Gln Glu Gln Asn Leu Gln Asn Lys Asp
465                 470                 475                 480 aaa aag aag aaa tcc aag ccc atc ttg tgt cca gcc ctc tct tcc ctg       1488
Lys Lys Lys Lys Ser Lys Pro Ile Leu Cys Pro Ala Leu Ser Ser Leu
            485                 490                 495 gtt atc tac ttg aag tct gtc tca ttc cgc agc ttc aca cat tca aag       1536
Val Ile Tyr Leu Lys Ser Val Ser Phe Arg Ser Phe Thr His Ser Lys
        500                 505                 510 gag cac tac cac ttc tac gag ata tca tct ttc tct gaa acc aag gcc       1584
Glu His Tyr His Phe Tyr Glu Ile Ser Ser Phe Ser Glu Thr Lys Ala
        515                 520                 525 aag cgc ctc atc aag gag gct ggc aat gag ttt gtg cag cac aat act       1632
Lys Arg Leu Ile Lys Glu Ala Gly Asn Glu Phe Val Gln His Asn Thr
530                 535                 540 tgg cag tta agc cgt gtg tat ccc agc ggc ctg agg aca gac tct tcc       1680
Trp Gln Leu Ser Arg Val Tyr Pro Ser Gly Leu Arg Thr Asp Ser Ser
545                 550                 555                 560 aac tac aac ccc cag gaa ctc tgg aat gca ggc tgc cag atg gtg gcc       1728
Asn Tyr Asn Pro Gln Glu Leu Trp Asn Ala Gly Cys Gln Met Val Ala
            565                 570                 575 atg aat atg cag act gca ggg ctt gaa atg gac atc tgt gat ggg cat       1776
Met Asn Met Gln Thr Ala Gly Leu Glu Met Asp Ile Cys Asp Gly His
        580                 585                 590 ttc cgc cag aat ggc ggc tgt ggc tat gtg ctg aag cca gac ttc ctg       1824
Phe Arg Gln Asn Gly Gly Cys Gly Tyr Val Leu Lys Pro Asp Phe Leu
        595                 600                 605 cgt gat atc cag agt tct ttc cac cct gag aag ccc atc agc cct ttc       1872
Arg Asp Ile Gln Ser Ser Phe His Pro Glu Lys Pro Ile Ser Pro Phe
610                 615                 620 aaa gcc cag act ctc tta atc cag gtg atc agc ggt cag caa ctc ccc       1920
Lys Ala Gln Thr Leu Leu Ile Gln Val Ile Ser Gly Gln Gln Leu Pro
625                 630                 635                 640 aaa gtg gac aag acc aaa gag ggg tcc att gtg gat cca ctg gtg aaa       1968
Lys Val Asp Lys Thr Lys Glu Gly Ser Ile Val Asp Pro Leu Val Lys
            645                 650                 655 gtg cag atc ttt ggc gtt cgt cta gac aca gca cgg cag gag acc aac       2016
Val Gln Ile Phe Gly Val Arg Leu Asp Thr Ala Arg Gln Glu Thr Asn
        660                 665                 670 tat gtg gag aac aat ggt ttt aat cca tac tgg ggg cag aca cta tgt       2064
Tyr Val Glu Asn Asn Gly Phe Asn Pro Tyr Trp Gly Gln Thr Leu Cys
        675                 680                 685 ttc cgg gtg ctg gtg cct gaa ctt gcc atg ctg cgt ttt gtg gta atg       2112
Phe Arg Val Leu Val Pro Glu Leu Ala Met Leu Arg Phe Val Val Met
```

```
                    690                 695                 700
gat tat gac tgg aaa tcc cga aat gac ttt att ggt cag tac acc ctg      2160
Asp Tyr Asp Trp Lys Ser Arg Asn Asp Phe Ile Gly Gln Tyr Thr Leu
705                 710                 715                 720 cct tgg acc tgc atg caa caa ggt tac cgc cac att cac ctg ctg tcc      2208
Pro Trp Thr Cys Met Gln Gln Gly Tyr Arg His Ile His Leu Leu Ser
                725                 730                 735 aaa gat ggc atc agc ctc cgc cca gct tcc atc ttt gtg tat atc tgc      2256
Lys Asp Gly Ile Ser Leu Arg Pro Ala Ser Ile Phe Val Tyr Ile Cys
            740                 745                 750 atc cag gaa ggc ctg gag ggg gat gag tcc tga                          2289
Ile Gln Glu Gly Leu Glu Gly Asp Glu Ser
        755                 760
```

<210> SEQ ID NO 2
<211> LENGTH: 762
<212> TYPE: PRT
<213> ORGANISM: Artificial Sequence
<220> FEATURE:
<223> OTHER INFORMATION: Description of Artificial Sequence: Primer 1

<400> SEQUENCE: 2

```
Met Ala Ser Leu Leu Gln Asp Gln Leu Thr Thr Asp Gln Asp Leu Leu
 1               5                   10                  15

Leu Met Gln Glu Gly Met Pro Met Arg Lys Val Arg Ser Lys Ser Trp
            20                  25                  30

Lys Lys Leu Arg Tyr Phe Arg Leu Gln Asn Asp Gly Met Thr Val Trp
        35                  40                  45

His Ala Arg Gln Ala Arg Gly Ser Ala Lys Pro Ser Phe Ser Ile Ser
    50                  55                  60

Asp Val Glu Thr Ile Arg Asn Gly His Asp Ser Glu Leu Leu Arg Ser
 65                  70                  75                  80

Leu Ala Glu Glu Leu Pro Leu Gly Gln Gly Phe Thr Ile Val Phe His
                85                  90                  95

Gly Arg Arg Ser Asn Leu Asp Leu Met Ala Asn Ser Val Glu Glu Ala
            100                 105                 110

Gln Ile Trp Met Arg Gly Leu Gln Leu Leu Val Asp Leu Val Thr Ser
        115                 120                 125

Met Asp His Gln Glu Arg Leu Asp Gln Trp Leu Ser Asp Trp Phe Gln
    130                 135                 140

Arg Gly Asp Lys Asn Gln Asp Gly Lys Met Ser Phe Gln Glu Val Gln
145                 150                 155                 160

Arg Leu Leu His Leu Met Asn Val Glu Met Asp Gln Glu Tyr Ala Phe
                165                 170                 175

Ser Leu Phe Gln Ala Ala Asp Thr Ser Gln Ser Gly Thr Leu Glu Gly
            180                 185                 190

Glu Glu Phe Val Gln Phe Tyr Lys Ala Leu Thr Lys Arg Ala Glu Val
        195                 200                 205

Gln Glu Leu Phe Glu Ser Phe Ser Ala Asp Gly Gln Lys Leu Thr Leu
    210                 215                 220

Leu Glu Phe Leu Asp Phe Leu Gln Glu Glu Gln Lys Glu Arg Asp Cys
225                 230                 235                 240

Thr Ser Glu Leu Ala Leu Glu Leu Ile Asp Arg Tyr Glu Pro Ser Asp
                245                 250                 255

Ser Gly Lys Leu Arg His Val Leu Ser Met Asp Gly Phe Leu Ser Tyr
            260                 265                 270
```

```
Leu Cys Ser Lys Asp Gly Asp Ile Phe Asn Pro Ala Cys Leu Pro Ile
        275                 280                 285

Tyr Gln Asp Met Thr Gln Pro Leu Asn His Tyr Phe Ile Cys Ser Ser
        290                 295                 300

His Asn Thr Tyr Leu Val Gly Asp Gln Leu Cys Gly Gln Ser Ser Val
305                 310                 315                 320

Glu Gly Tyr Ile Arg Ala Leu Lys Arg Gly Cys Arg Cys Val Glu Val
                325                 330                 335

Asp Val Trp Asp Gly Pro Ser Gly Glu Pro Val Val Tyr His Gly His
            340                 345                 350

Thr Leu Thr Ser Arg Ile Leu Phe Lys Asp Val Val Ala Thr Val Ala
        355                 360                 365

Gln Tyr Ala Phe Gln Thr Ser Asp Tyr Pro Val Ile Leu Ser Leu Glu
        370                 375                 380

Thr His Cys Ser Trp Glu Gln Gln Gln Thr Met Ala Arg His Leu Thr
385                 390                 395                 400

Glu Ile Leu Gly Glu Gln Leu Leu Ser Thr Thr Leu Asp Gly Val Leu
                405                 410                 415

Pro Thr Gln Leu Pro Ser Pro Glu Glu Leu Arg Arg Lys Ile Leu Val
            420                 425                 430

Lys Gly Lys Lys Leu Thr Leu Glu Glu Asp Leu Glu Tyr Glu Glu Glu
        435                 440                 445

Glu Ala Glu Pro Glu Leu Glu Glu Ser Glu Leu Ala Leu Glu Ser Gln
    450                 455                 460

Phe Glu Thr Glu Pro Glu Pro Gln Glu Gln Asn Leu Gln Asn Lys Asp
465                 470                 475                 480

Lys Lys Lys Lys Ser Lys Pro Ile Leu Cys Pro Ala Leu Ser Ser Leu
                485                 490                 495

Val Ile Tyr Leu Lys Ser Val Ser Phe Arg Ser Phe Thr His Ser Lys
            500                 505                 510

Glu His Tyr His Phe Tyr Glu Ile Ser Ser Phe Ser Glu Thr Lys Ala
        515                 520                 525

Lys Arg Leu Ile Lys Glu Ala Gly Asn Glu Phe Val Gln His Asn Thr
        530                 535                 540

Trp Gln Leu Ser Arg Val Tyr Pro Ser Gly Leu Arg Thr Asp Ser Ser
545                 550                 555                 560

Asn Tyr Asn Pro Gln Glu Leu Trp Asn Ala Gly Cys Gln Met Val Ala
                565                 570                 575

Met Asn Met Gln Thr Ala Gly Leu Glu Met Asp Ile Cys Asp Gly His
            580                 585                 590

Phe Arg Gln Asn Gly Gly Cys Gly Tyr Val Leu Lys Pro Asp Phe Leu
        595                 600                 605

Arg Asp Ile Gln Ser Ser Phe His Pro Glu Lys Pro Ile Ser Pro Phe
610                 615                 620

Lys Ala Gln Thr Leu Leu Ile Gln Val Ile Ser Gly Gln Gln Leu Pro
625                 630                 635                 640

Lys Val Asp Lys Thr Lys Glu Gly Ser Ile Val Asp Pro Leu Val Lys
                645                 650                 655

Val Gln Ile Phe Gly Val Arg Leu Asp Thr Ala Arg Gln Glu Thr Asn
            660                 665                 670

Tyr Val Glu Asn Asn Gly Phe Asn Pro Tyr Trp Gly Gln Thr Leu Cys
        675                 680                 685

Phe Arg Val Leu Val Pro Glu Leu Ala Met Leu Arg Phe Val Val Met
```

|   |   |   |   |   |   |   |   |   |   |   |   |   |
|---|---|---|---|---|---|---|---|---|---|---|---|---|
| | | | 690 | | | | 695 | | | | 700 | |
| Asp | Tyr | Asp | Trp | Lys | Ser | Arg | Asn | Asp | Phe | Ile | Gly | Gln | Tyr | Thr | Leu |
| 705 | | | | | 710 | | | | | 715 | | | | | 720 |

Pro Trp Thr Cys Met Gln Gln Gly Tyr Arg His Ile His Leu Leu Ser
                       725                       730                       735

Lys Asp Gly Ile Ser Leu Arg Pro Ala Ser Ile Phe Val Tyr Ile Cys
               740                       745                       750

Ile Gln Glu Gly Leu Glu Gly Asp Glu Ser
        755                       760

<210> SEQ ID NO 3
<211> LENGTH: 2540
<212> TYPE: DNA
<213> ORGANISM: Homo sapiens
<220> FEATURE:
<221> NAME/KEY: CDS
<222> LOCATION: (59)..(2416)

<400> SEQUENCE: 3
cctttgctct tccttgctcc tttaggtgat ctggtgccag ctggtggaac agtgggtg     58 atg gcg tcc ctg ctg caa gac cag ctg acc act gat cag gac ttg ctg    106
Met Ala Ser Leu Leu Gln Asp Gln Leu Thr Thr Asp Gln Asp Leu Leu
  1               5                 10                15 ctg atg cag gaa ggc atg ccg atg cgc aag gtg agg tcc aaa agc tgg    154
Leu Met Gln Glu Gly Met Pro Met Arg Lys Val Arg Ser Lys Ser Trp
            20                 25                30 aag aag cta aga tac ttc aga ctt cag aat gac ggc atg aca gtc tgg    202
Lys Lys Leu Arg Tyr Phe Arg Leu Gln Asn Asp Gly Met Thr Val Trp
               35                 40              45 cat gca cgg cag gcc agg ggc agt gcc aag ccc agc ttc tca atc tct    250
His Ala Arg Gln Ala Arg Gly Ser Ala Lys Pro Ser Phe Ser Ile Ser
 50                 55                 60 gat gtg gag aca ata cgt aat ggc cat gat tcc gag ttg ctg cgt agc    298
Asp Val Glu Thr Ile Arg Asn Gly His Asp Ser Glu Leu Leu Arg Ser
 65                 70                 75              80 ctg gca gag gag ctc ccc ctg gag cag ggc ttc acc att gtc ttc cat    346
Leu Ala Glu Glu Leu Pro Leu Glu Gln Gly Phe Thr Ile Val Phe His
                       85                 90              95 ggc cgc cgc tcc aac ctg gac ctg atg gcc aac agt gtt gag gag gcc    394
Gly Arg Arg Ser Asn Leu Asp Leu Met Ala Asn Ser Val Glu Glu Ala
            100                105               110 cag ata tgg atg cga ggg ctc cag ctg ttg gtg gat ctt gtc acc agc    442
Gln Ile Trp Met Arg Gly Leu Gln Leu Leu Val Asp Leu Val Thr Ser
               115               120              125 atg gac cat cag gag cgc ctg gac cac gat tgg ttt caa cgt gga gac    490
Met Asp His Gln Glu Arg Leu Asp His Asp Trp Phe Gln Arg Gly Asp
 130                135               140 aaa aat cag gat ggt aag atg agt ttc caa gaa gtt cag cgg tta ttg    538
Lys Asn Gln Asp Gly Lys Met Ser Phe Gln Glu Val Gln Arg Leu Leu
145                150               155              160 cac cta atg aat gtg gaa atg gac caa gaa tat gcc ttc agt ctt ttt    586
His Leu Met Asn Val Glu Met Asp Gln Glu Tyr Ala Phe Ser Leu Phe
               165               170              175 cag gca gca gac acg tcc cag tct gga acc ctg gaa gga gaa gaa ttc    634
Gln Ala Ala Asp Thr Ser Gln Ser Gly Thr Leu Glu Gly Glu Glu Phe
            180                185               190 gta cag ttc tat aag gca ttg act aaa cgt gct gag gtg cag gaa ctg    682
Val Gln Phe Tyr Lys Ala Leu Thr Lys Arg Ala Glu Val Gln Glu Leu
               195               200              205

```
ttt gaa agt ttt tca gct gat ggg cag aag ctg act ctg ctg gaa ttt    730
Phe Glu Ser Phe Ser Ala Asp Gly Gln Lys Leu Thr Leu Leu Glu Phe
    210             215                 220 ttg gat ttc ctc caa gag gag cag aag gag aga gac tgc acc tct gag    778
Leu Asp Phe Leu Gln Glu Glu Gln Lys Glu Arg Asp Cys Thr Ser Glu
225             230                 235                 240 ctt gct ctg gaa ctc att gac cgc tat gaa cct tca gac agt ggc aaa    826
Leu Ala Leu Glu Leu Ile Asp Arg Tyr Glu Pro Ser Asp Ser Gly Lys
                245                 250                 255 ctg cgg cat gtg ctg agt atg gat ggc ttc ctc agc tac ctc tgc tct    874
Leu Arg His Val Leu Ser Met Asp Gly Phe Leu Ser Tyr Leu Cys Ser
            260                 265                 270 aag gat gga gac atc ttc aac cca gcc tgc ctc ccc atc tat cag gat    922
Lys Asp Gly Asp Ile Phe Asn Pro Ala Cys Leu Pro Ile Tyr Gln Asp
        275                 280                 285 atg act caa ccc ctg aac cac tac ttc atc tgc tct tct cat aac acc    970
Met Thr Gln Pro Leu Asn His Tyr Phe Ile Cys Ser Ser His Asn Thr
    290                 295                 300 tac cta gtg ggg gac cag ctt tgt ggc cag agc agc gtc gag gga tat   1018
Tyr Leu Val Gly Asp Gln Leu Cys Gly Gln Ser Ser Val Glu Gly Tyr
305             310                 315                 320 ata cgg gcc ctg aag cgg ggg tgc cgc tgc gtg gag gtg gat gta tgg   1066
Ile Arg Ala Leu Lys Arg Gly Cys Arg Cys Val Glu Val Asp Val Trp
                325                 330                 335 gat gga cct agc ggg gaa cct gtc gtt tac cac gga cac acc ctg acc   1114
Asp Gly Pro Ser Gly Glu Pro Val Val Tyr His Gly His Thr Leu Thr
            340                 345                 350 tcc cgc atc ctg ttc aaa gat gtc gtg gcc aca gta gca cag tat gcc   1162
Ser Arg Ile Leu Phe Lys Asp Val Val Ala Thr Val Ala Gln Tyr Ala
        355                 360                 365 ttc cag aca tca gac tac cca gtc atc ttg tcc ctg gag acc cac tgc   1210
Phe Gln Thr Ser Asp Tyr Pro Val Ile Leu Ser Leu Glu Thr His Cys
    370                 375                 380 agc tgg gag cag cag cag acc atg gcc cgt cat ctg act gag atc ctg   1258
Ser Trp Glu Gln Gln Gln Thr Met Ala Arg His Leu Thr Glu Ile Leu
385             390                 395                 400 ggg gag cag ctg ctg agc acc acc ttg gat ggg gtg ctg ccc act cag   1306
Gly Glu Gln Leu Leu Ser Thr Thr Leu Asp Gly Val Leu Pro Thr Gln
                405                 410                 415 ctg ccc tcg cct gag ctt cgg agg aag atc ctg gtg aag ggg aag aag   1354
Leu Pro Ser Pro Glu Leu Arg Arg Lys Ile Leu Val Lys Gly Lys Lys
            420                 425                 430 tta aca ctt gag gaa gac ctg gaa tat gag gaa gag gaa gca gaa cct   1402
Leu Thr Leu Glu Glu Asp Leu Glu Tyr Glu Glu Glu Glu Ala Glu Pro
        435                 440                 445 gag ttg gaa gag tca gaa ttg gcg ctg gag tcc cag ttt gag act gag   1450
Glu Leu Glu Glu Ser Glu Leu Ala Leu Glu Ser Gln Phe Glu Thr Glu
    450                 455                 460 cct gag ccc cag gag cag aac ctt cag aat aag gac aaa aag aag aaa   1498
Pro Glu Pro Gln Glu Gln Asn Leu Gln Asn Lys Asp Lys Lys Lys Lys
465             470                 475                 480 tcc aag ccc atc ttg tgt cca gcc ctc tct tcc ctg gtt atc tac ttg   1546
Ser Lys Pro Ile Leu Cys Pro Ala Leu Ser Ser Leu Val Ile Tyr Leu
                485                 490                 495 aag tct gtc tca ttc cgc agc ttc aca cat tca aag gag cac tac cac   1594
Lys Ser Val Ser Phe Arg Ser Phe Thr His Ser Lys Glu His Tyr His
            500                 505                 510 ttc tac gag ata tca tct ttc tct gaa acc aag gcc aag cgc ctc atc   1642
Phe Tyr Glu Ile Ser Ser Phe Ser Glu Thr Lys Ala Lys Arg Leu Ile
        515                 520                 525
```

```
aag gag gct ggc aat gag ttt gtg cag cac aat act tgg cag tta agc    1690
Lys Glu Ala Gly Asn Glu Phe Val Gln His Asn Thr Trp Gln Leu Ser
            530                 535                 540 cgt gtg tat ccc agc ggc ctg agg aca gac tct tcc aac tac tac aac    1738
Arg Val Tyr Pro Ser Gly Leu Arg Thr Asp Ser Ser Asn Tyr Tyr Asn
545                 550                 555                 560 ccc cag gaa ctc tgg aat gca ggc tgc cag atg gtg gcc atg aat atg    1786
Pro Gln Glu Leu Trp Asn Ala Gly Cys Gln Met Val Ala Met Asn Met
                565                 570                 575 cag act gca ggg ctt gaa atg gac atc tgt gat ggg cat ttc cgc cag    1834
Gln Thr Ala Gly Leu Glu Met Asp Ile Cys Asp Gly His Phe Arg Gln
            580                 585                 590 aat ggc ggc tgt ggc tat gtg ctg aag cca gac ttc ctg cgt gat atc    1882
Asn Gly Gly Cys Gly Tyr Val Leu Lys Pro Asp Phe Leu Arg Asp Ile
        595                 600                 605 cag agt tct ttc cac cct gag aag ccc atc agc cct ttc aaa gcc cag    1930
Gln Ser Ser Phe His Pro Glu Lys Pro Ile Ser Pro Phe Lys Ala Gln
    610                 615                 620 act ctc tta aac cag gtg atc agc gtt cag caa ctc ccc aaa gtg gac    1978
Thr Leu Leu Asn Gln Val Ile Ser Val Gln Gln Leu Pro Lys Val Asp
625                 630                 635                 640 aag acc aaa gag ggg tcc att gtg gat cca ctg gtg aaa gtg cag atc    2026
Lys Thr Lys Glu Gly Ser Ile Val Asp Pro Leu Val Lys Val Gln Ile
                645                 650                 655 ttt ggc gtt cgt cta gac aca gca cgg cag gag acc aac tat gtg gag    2074
Phe Gly Val Arg Leu Asp Thr Ala Arg Gln Glu Thr Asn Tyr Val Glu
            660                 665                 670 aac aat ggt ttt aat cca tac tgg ggg cag aca cta tgt ttc cgg gtg    2122
Asn Asn Gly Phe Asn Pro Tyr Trp Gly Gln Thr Leu Cys Phe Arg Val
        675                 680                 685 ctg gtg cct gaa ctt gcc atg ctg cgt ttt gtg gta atg gat tat gac    2170
Leu Val Pro Glu Leu Ala Met Leu Arg Phe Val Val Met Asp Tyr Asp
    690                 695                 700 tgg aaa tcc cga aat gac ttt att ggt cag tac acc ctg cct tgg acc    2218
Trp Lys Ser Arg Asn Asp Phe Ile Gly Gln Tyr Thr Leu Pro Trp Thr
705                 710                 715                 720 tgc atg caa caa ggt gag cca gcc cct ttg gcc cct ggc caa tac ccc    2266
Cys Met Gln Gln Gly Glu Pro Ala Pro Leu Ala Pro Gly Gln Tyr Pro
                725                 730                 735 agc tct ggc tgc ctt cct aat gct gtc ctc ctg ccc ctt cca ggt tac    2314
Ser Ser Gly Cys Leu Pro Asn Ala Val Leu Leu Pro Leu Pro Gly Tyr
            740                 745                 750 cgc cac att cac ctg ctg tcc aaa gat ggc atc agc ctc cgc cca gct    2362
Arg His Ile His Leu Leu Ser Lys Asp Gly Ile Ser Leu Arg Pro Ala
        755                 760                 765 tcc atc ttt gtg tat atc tgc atc cag gaa ggc ctg gag ggg gat gag    2410
Ser Ile Phe Val Tyr Ile Cys Ile Gln Glu Gly Leu Glu Gly Asp Glu
    770                 775                 780 tcc tga ggtgggcatt tcacgggaag ggttggtgtg ctggctttag acggggagaa    2466
Ser
785 acatctggaa ggatgctcga gagaacaaat ggaggtggtg aaaatcaagc tttggattgt    2526 gcattcctag gcac                                                      2540

<210> SEQ ID NO 4
<211> LENGTH: 785
<212> TYPE: PRT
<213> ORGANISM: Homo sapiens
```

```
<400> SEQUENCE: 4

Met Ala Ser Leu Leu Gln Asp Gln Leu Thr Thr Asp Gln Asp Leu Leu
 1               5                  10                  15

Leu Met Gln Glu Gly Met Pro Met Arg Lys Val Arg Ser Lys Ser Trp
            20                  25                  30

Lys Lys Leu Arg Tyr Phe Arg Leu Gln Asn Asp Gly Met Thr Val Trp
        35                  40                  45

His Ala Arg Gln Ala Arg Gly Ser Ala Lys Pro Ser Phe Ser Ile Ser
    50                  55                  60

Asp Val Glu Thr Ile Arg Asn Gly His Asp Ser Glu Leu Leu Arg Ser
 65                  70                  75                  80

Leu Ala Glu Glu Leu Pro Leu Glu Gln Gly Phe Thr Ile Val Phe His
                85                  90                  95

Gly Arg Arg Ser Asn Leu Asp Leu Met Ala Asn Ser Val Glu Glu Ala
            100                 105                 110

Gln Ile Trp Met Arg Gly Leu Gln Leu Leu Val Asp Leu Val Thr Ser
        115                 120                 125

Met Asp His Gln Glu Arg Leu Asp His Asp Trp Phe Gln Arg Gly Asp
130                 135                 140

Lys Asn Gln Asp Gly Lys Met Ser Phe Gln Glu Val Gln Arg Leu Leu
145                 150                 155                 160

His Leu Met Asn Val Glu Met Asp Gln Glu Tyr Ala Phe Ser Leu Phe
                165                 170                 175

Gln Ala Ala Asp Thr Ser Gln Ser Gly Thr Leu Glu Gly Glu Glu Phe
            180                 185                 190

Val Gln Phe Tyr Lys Ala Leu Thr Lys Arg Ala Glu Val Gln Glu Leu
        195                 200                 205

Phe Glu Ser Phe Ser Ala Asp Gly Gln Lys Leu Thr Leu Leu Glu Phe
    210                 215                 220

Leu Asp Phe Leu Gln Glu Gln Lys Glu Arg Asp Cys Thr Ser Glu
225                 230                 235                 240

Leu Ala Leu Glu Leu Ile Asp Arg Tyr Glu Pro Ser Asp Ser Gly Lys
                245                 250                 255

Leu Arg His Val Leu Ser Met Asp Gly Phe Leu Ser Tyr Leu Cys Ser
            260                 265                 270

Lys Asp Gly Asp Ile Phe Asn Pro Ala Cys Leu Pro Ile Tyr Gln Asp
        275                 280                 285

Met Thr Gln Pro Leu Asn His Tyr Phe Ile Cys Ser Ser His Asn Thr
    290                 295                 300

Tyr Leu Val Gly Asp Gln Leu Cys Gly Gln Ser Ser Val Glu Gly Tyr
305                 310                 315                 320

Ile Arg Ala Leu Lys Arg Gly Cys Arg Cys Val Glu Val Asp Val Trp
                325                 330                 335

Asp Gly Pro Ser Gly Glu Pro Val Val Tyr His Gly His Thr Leu Thr
            340                 345                 350

Ser Arg Ile Leu Phe Lys Asp Val Val Ala Thr Val Ala Gln Tyr Ala
        355                 360                 365

Phe Gln Thr Ser Asp Tyr Pro Val Ile Leu Ser Leu Glu Thr His Cys
    370                 375                 380

Ser Trp Glu Gln Gln Gln Thr Met Ala Arg His Leu Thr Glu Ile Leu
385                 390                 395                 400

Gly Glu Gln Leu Leu Ser Thr Thr Leu Asp Gly Val Leu Pro Thr Gln
                405                 410                 415
```

```
Leu Pro Ser Pro Glu Leu Arg Arg Lys Ile Leu Val Lys Gly Lys Lys
            420                 425                 430

Leu Thr Leu Glu Glu Asp Leu Glu Tyr Glu Glu Glu Ala Glu Pro
        435                 440                 445

Glu Leu Glu Glu Ser Glu Leu Ala Leu Glu Ser Gln Phe Glu Thr Glu
    450                 455                 460

Pro Glu Pro Gln Glu Gln Asn Leu Gln Asn Lys Asp Lys Lys Lys
465                 470                 475                 480

Ser Lys Pro Ile Leu Cys Pro Ala Leu Ser Ser Leu Val Ile Tyr Leu
            485                 490                 495

Lys Ser Val Ser Phe Arg Ser Phe Thr His Ser Lys Glu His Tyr His
        500                 505                 510

Phe Tyr Glu Ile Ser Ser Phe Ser Glu Thr Lys Ala Lys Arg Leu Ile
    515                 520                 525

Lys Glu Ala Gly Asn Glu Phe Val Gln His Asn Thr Trp Gln Leu Ser
    530                 535                 540

Arg Val Tyr Pro Ser Gly Leu Arg Thr Asp Ser Ser Asn Tyr Tyr Asn
545                 550                 555                 560

Pro Gln Glu Leu Trp Asn Ala Gly Cys Gln Met Val Ala Met Asn Met
            565                 570                 575

Gln Thr Ala Gly Leu Glu Met Asp Ile Cys Asp Gly His Phe Arg Gln
        580                 585                 590

Asn Gly Gly Cys Gly Tyr Val Leu Lys Pro Asp Phe Leu Arg Asp Ile
    595                 600                 605

Gln Ser Ser Phe His Pro Glu Lys Pro Ile Ser Pro Phe Lys Ala Gln
    610                 615                 620

Thr Leu Leu Asn Gln Val Ile Ser Val Gln Gln Leu Pro Lys Val Asp
625                 630                 635                 640

Lys Thr Lys Glu Gly Ser Ile Val Asp Pro Leu Val Lys Val Gln Ile
            645                 650                 655

Phe Gly Val Arg Leu Asp Thr Ala Arg Gln Glu Thr Asn Tyr Val Glu
        660                 665                 670

Asn Asn Gly Phe Asn Pro Tyr Trp Gly Gln Thr Leu Cys Phe Arg Val
    675                 680                 685

Leu Val Pro Glu Leu Ala Met Leu Arg Phe Val Val Met Asp Tyr Asp
    690                 695                 700

Trp Lys Ser Arg Asn Asp Phe Ile Gly Gln Tyr Thr Leu Pro Trp Thr
705                 710                 715                 720

Cys Met Gln Gln Gly Glu Pro Ala Pro Leu Ala Pro Gly Gln Tyr Pro
            725                 730                 735

Ser Ser Gly Cys Leu Pro Asn Ala Val Leu Leu Pro Leu Pro Gly Tyr
        740                 745                 750

Arg His Ile His Leu Leu Ser Lys Asp Gly Ile Ser Leu Arg Pro Ala
    755                 760                 765

Ser Ile Phe Val Tyr Ile Cys Ile Gln Glu Gly Leu Glu Gly Asp Glu
    770                 775                 780

Ser
785

<210> SEQ ID NO 5
<211> LENGTH: 2462
<212> TYPE: DNA
<213> ORGANISM: Homo sapiens
<220> FEATURE:
```

```
<221> NAME/KEY: CDS
<222> LOCATION: (59)..(2338)

<400> SEQUENCE: 5
cctttgctct tccttgctcc tttaggtgat ctggtgccag ctggtggaac agtgggtg          58 atg gcg tcc ctg ctg caa gac cag ctg acc act gat cag gac ttg ctg        106
Met Ala Ser Leu Leu Gln Asp Gln Leu Thr Thr Asp Gln Asp Leu Leu
 1               5                  10                  15 ctg atg cag gaa ggc atg ccg atg cgc aag gtg agg tcc aaa agc tgg        154
Leu Met Gln Glu Gly Met Pro Met Arg Lys Val Arg Ser Lys Ser Trp
                 20                  25                  30 aag aag cta aga tac ttc aga ctt cag aat gac ggc atg aca gtc tgg        202
Lys Lys Leu Arg Tyr Phe Arg Leu Gln Asn Asp Gly Met Thr Val Trp
             35                  40                  45 cat gca cgg cag gcc agg ggc agt gcc aag ccc agc ttc tca atc tct        250
His Ala Arg Gln Ala Arg Gly Ser Ala Lys Pro Ser Phe Ser Ile Ser
         50                  55                  60 gat gtg gag aca ata cgt aat ggc cat gat tcc gag ttg ctg cgt agc        298
Asp Val Glu Thr Ile Arg Asn Gly His Asp Ser Glu Leu Leu Arg Ser
 65                  70                  75                  80 ctg gca gag gag ctc ccc ctg gag cag ggc ttc acc att gtc ttc cat        346
Leu Ala Glu Glu Leu Pro Leu Glu Gln Gly Phe Thr Ile Val Phe His
                 85                  90                  95 ggc cgc cgc tcc aac ctg gac ctg atg gcc aac agt gtt gag gag gcc        394
Gly Arg Arg Ser Asn Leu Asp Leu Met Ala Asn Ser Val Glu Glu Ala
                100                 105                 110 cag ata tgg atg cga ggg ctc cag ctg ttg gtg gat ctt gtc acc agc        442
Gln Ile Trp Met Arg Gly Leu Gln Leu Leu Val Asp Leu Val Thr Ser
            115                 120                 125 atg gac cat cag gag cgc ctg gac cac gat tgg ttt caa cgt gga gac        490
Met Asp His Gln Glu Arg Leu Asp His Asp Trp Phe Gln Arg Gly Asp
130                 135                 140 aaa aat cag gat ggt aag atg agt ttc caa gaa gtt cag cgg tta ttg        538
Lys Asn Gln Asp Gly Lys Met Ser Phe Gln Glu Val Gln Arg Leu Leu
145                 150                 155                 160 cac cta atg aat gtg gaa atg gac caa gaa tat gcc ttc agt ctt ttt        586
His Leu Met Asn Val Glu Met Asp Gln Glu Tyr Ala Phe Ser Leu Phe
                165                 170                 175 cag gca gca gac acg tcc cag tct gga acc ctg gaa gga gaa gaa ttc        634
Gln Ala Ala Asp Thr Ser Gln Ser Gly Thr Leu Glu Gly Glu Glu Phe
            180                 185                 190 gta cag ttc tat aag gca ttg act aaa cgt gct gag gtg cag gaa ctg        682
Val Gln Phe Tyr Lys Ala Leu Thr Lys Arg Ala Glu Val Gln Glu Leu
        195                 200                 205 ttt gaa agt ttt tca gct gat ggg cag aag ctg act ctg ctg gaa ttt        730
Phe Glu Ser Phe Ser Ala Asp Gly Gln Lys Leu Thr Leu Leu Glu Phe
    210                 215                 220 ttg gat ttc ctc caa gag gag cag aag gag aga gac tgc acc tct gag        778
Leu Asp Phe Leu Gln Glu Glu Gln Lys Glu Arg Asp Cys Thr Ser Glu
225                 230                 235                 240 ctt gct ctg gaa ctc att gac cgc tat gaa cct tca gac agt ggc aaa        826
Leu Ala Leu Glu Leu Ile Asp Arg Tyr Glu Pro Ser Asp Ser Gly Lys
                245                 250                 255 ctg cgg cat gtg ctg agt atg gat ggc ttc ctc agc tac ctc tgc tct        874
Leu Arg His Val Leu Ser Met Asp Gly Phe Leu Ser Tyr Leu Cys Ser
            260                 265                 270 aag gat gga gac atc ttc aac cca gcc tgc ctc ccc atc tat cag gat        922
Lys Asp Gly Asp Ile Phe Asn Pro Ala Cys Leu Pro Ile Tyr Gln Asp
        275                 280                 285
```

```
atg act caa ccc ctg aac cac tac ttc atc tgc tct tct cat aac acc       970
Met Thr Gln Pro Leu Asn His Tyr Phe Ile Cys Ser Ser His Asn Thr
290                 295                 300 tac cta gtg ggg gac cag ctt tgt ggc cag agc agc gtc gag gga tat      1018
Tyr Leu Val Gly Asp Gln Leu Cys Gly Gln Ser Ser Val Glu Gly Tyr
305                 310                 315                 320 ata cgg gcc ctg aag cgg ggg tgc cgc tgc gtg gag gtg gat gta tgg      1066
Ile Arg Ala Leu Lys Arg Gly Cys Arg Cys Val Glu Val Asp Val Trp
                325                 330                 335 gat gga cct agc ggg gaa cct gtc gtt tac cac gga cac acc ctg acc      1114
Asp Gly Pro Ser Gly Glu Pro Val Val Tyr His Gly His Thr Leu Thr
            340                 345                 350 tcc cgc atc ctg ttc aaa gat gtc gtg gcc aca gta gca cag tat gcc      1162
Ser Arg Ile Leu Phe Lys Asp Val Val Ala Thr Val Ala Gln Tyr Ala
                355                 360                 365 ttc cag aca tca gac tac cca gtc atc ttg tcc ctg gag acc cac tgc      1210
Phe Gln Thr Ser Asp Tyr Pro Val Ile Leu Ser Leu Glu Thr His Cys
370                 375                 380 agc tgg gag cag cag cag acc atg gcc cgt cat ctg act gag atc ctg      1258
Ser Trp Glu Gln Gln Gln Thr Met Ala Arg His Leu Thr Glu Ile Leu
385                 390                 395                 400 ggg gag cag ctg ctg agc acc acc ttg gat ggg gtg ctg ccc act cag      1306
Gly Glu Gln Leu Leu Ser Thr Thr Leu Asp Gly Val Leu Pro Thr Gln
                405                 410                 415 ctg ccc tcg cct gag ctt cgg agg aag atc ctg gtg aag ggg aag aag      1354
Leu Pro Ser Pro Glu Leu Arg Arg Lys Ile Leu Val Lys Gly Lys Lys
            420                 425                 430 tta aca ctt gag gaa gac ctg gaa tat gag gaa gag gaa gca gaa cct      1402
Leu Thr Leu Glu Glu Asp Leu Glu Tyr Glu Glu Glu Glu Ala Glu Pro
                435                 440                 445 gag ttg gaa gag tca gaa ttg gcg ctg gag tcc cag ttt gag act gag      1450
Glu Leu Glu Glu Ser Glu Leu Ala Leu Glu Ser Gln Phe Glu Thr Glu
450                 455                 460 cct gag ccc cag gag cag aac ctt cag aat aag gac aaa aag aag aaa      1498
Pro Glu Pro Gln Glu Gln Asn Leu Gln Asn Lys Asp Lys Lys Lys Lys
465                 470                 475                 480 tcc aag ccc atc ttg tgt cca gcc ctc tct ccc tgc gtt atc tac ttg      1546
Ser Lys Pro Ile Leu Cys Pro Ala Leu Ser Pro Cys Val Ile Tyr Leu
                485                 490                 495 aag tct gtc tca ttc cgc agc ttc aca cat tca aag gag cac tac cac      1594
Lys Ser Val Ser Phe Arg Ser Phe Thr His Ser Lys Glu His Tyr His
            500                 505                 510 ttc tac gag ata tca tct ttc tct gaa acc aag gcc aag cgc ctc atc      1642
Phe Tyr Glu Ile Ser Ser Phe Ser Glu Thr Lys Ala Lys Arg Leu Ile
                515                 520                 525 aag gag gct ggc aat gag ttt gtg cag cac aat act tgg cag tta agc      1690
Lys Glu Ala Gly Asn Glu Phe Val Gln His Asn Thr Trp Gln Leu Ser
530                 535                 540 cgt gtg tat ccc agc ggc ctg agg aca gac tct tcc aac tac tac aac      1738
Arg Val Tyr Pro Ser Gly Leu Arg Thr Asp Ser Ser Asn Tyr Tyr Asn
545                 550                 555                 560 ccc cag gaa ctc tgg aat gca ggc tgc cag atg gtg gcc atg aat atg      1786
Pro Gln Glu Leu Trp Asn Ala Gly Cys Gln Met Val Ala Met Asn Met
                565                 570                 575 cag act gca ggg ctt gaa atg gac atc tgt gat ggg cat ttc cgc cag      1834
Gln Thr Ala Gly Leu Glu Met Asp Ile Cys Asp Gly His Phe Arg Gln
            580                 585                 590 aat ggc ggc tgt ggc tat gtg ctg aag cca gac ttc ctg cgt gat atc      1882
Asn Gly Gly Cys Gly Tyr Val Leu Lys Pro Asp Phe Leu Arg Asp Ile
                595                 600                 605
```

```
cag agt tct ttc cac cct gag aag ccc atc agc cct ttc aaa gcc cag      1930
Gln Ser Ser Phe His Pro Glu Lys Pro Ile Ser Pro Phe Lys Ala Gln
    610                 615                 620 act ctc tta aac cag gtg atc agc gtt cag caa ctc ccc aaa gtg gac      1978
Thr Leu Leu Asn Gln Val Ile Ser Val Gln Gln Leu Pro Lys Val Asp
625                 630                 635                 640 aag acc aaa gag ggg tcc att gtg gat cca ctg gtg aaa gtg cag atc      2026
Lys Thr Lys Glu Gly Ser Ile Val Asp Pro Leu Val Lys Val Gln Ile
                645                 650                 655 ttt ggc gtt cgt cta gac aca gca cgg cag gag acc aac tat gtg gag      2074
Phe Gly Val Arg Leu Asp Thr Ala Arg Gln Glu Thr Asn Tyr Val Glu
            660                 665                 670 aac aat ggt ttt aat cca tac tgg ggg cag aca cta tgt ttc cgg gtg      2122
Asn Asn Gly Phe Asn Pro Tyr Trp Gly Gln Thr Leu Cys Phe Arg Val
        675                 680                 685 ctg gtg cct gaa ctt gcc atg ctg cgt ttt gtg gta atg gat tat gac      2170
Leu Val Pro Glu Leu Ala Met Leu Arg Phe Val Val Met Asp Tyr Asp
    690                 695                 700 tgg aaa tcc cga aat gac ttt att ggt cag tac acc ctg cct tgg acc      2218
Trp Lys Ser Arg Asn Asp Phe Ile Gly Gln Tyr Thr Leu Pro Trp Thr
705                 710                 715                 720 tgc atg caa caa ggt tac cgc cac att cac ctg ctg tcc aaa gat ggc      2266
Cys Met Gln Gln Gly Tyr Arg His Ile His Leu Leu Ser Lys Asp Gly
                725                 730                 735 atc agc ctc cgc cca gct tcc atc ttt gtg tat atc tgc atc cag gaa      2314
Ile Ser Leu Arg Pro Ala Ser Ile Phe Val Tyr Ile Cys Ile Gln Glu
            740                 745                 750 ggc ctg gag ggg gat gag tcc tga ggtgggcatt tcacgggaag ggttggtgtg    2368
Gly Leu Glu Gly Asp Glu Ser
        755                 760 ctggctttag acgggagaa acatctggaa ggatgctcga gagaacaaat ggaggtggtg     2428
aaaatcaagc tttggattgt gcattcctag gcac                                2462

<210> SEQ ID NO 6
<211> LENGTH: 759
<212> TYPE: PRT
<213> ORGANISM: Homo sapiens

<400> SEQUENCE: 6

Met Ala Ser Leu Leu Gln Asp Gln Leu Thr Thr Asp Gln Asp Leu Leu
 1               5                  10                  15

Leu Met Gln Glu Gly Met Pro Met Arg Lys Val Arg Ser Lys Ser Trp
            20                  25                  30

Lys Lys Leu Arg Tyr Phe Arg Leu Gln Asn Asp Gly Met Thr Val Trp
        35                  40                  45

His Ala Arg Gln Ala Arg Gly Ser Ala Lys Pro Ser Phe Ser Ile Ser
    50                  55                  60

Asp Val Glu Thr Ile Arg Asn Gly His Asp Ser Glu Leu Leu Arg Ser
65                  70                  75                  80

Leu Ala Glu Glu Leu Pro Leu Glu Gln Gly Phe Thr Ile Val Phe His
                85                  90                  95

Gly Arg Arg Ser Asn Leu Asp Leu Met Ala Asn Ser Val Glu Glu Ala
            100                 105                 110

Gln Ile Trp Met Arg Gly Leu Gln Leu Leu Val Asp Leu Val Thr Ser
        115                 120                 125

Met Asp His Gln Glu Arg Leu Asp His Asp Trp Phe Gln Arg Gly Asp
    130                 135                 140
```

-continued

```
Lys Asn Gln Asp Gly Lys Met Ser Phe Gln Glu Val Gln Arg Leu Leu
145                 150                 155                 160

His Leu Met Asn Val Glu Met Asp Gln Glu Tyr Ala Phe Ser Leu Phe
                165                 170                 175

Gln Ala Ala Asp Thr Ser Gln Ser Gly Thr Leu Glu Gly Glu Glu Phe
            180                 185                 190

Val Gln Phe Tyr Lys Ala Leu Thr Lys Arg Ala Glu Val Gln Glu Leu
        195                 200                 205

Phe Glu Ser Phe Ser Ala Asp Gly Gln Lys Leu Thr Leu Leu Glu Phe
    210                 215                 220

Leu Asp Phe Leu Gln Glu Gln Lys Glu Arg Asp Cys Thr Ser Glu
225                 230                 235                 240

Leu Ala Leu Glu Leu Ile Asp Arg Tyr Glu Pro Ser Asp Ser Gly Lys
                245                 250                 255

Leu Arg His Val Leu Ser Met Asp Gly Phe Leu Ser Tyr Leu Cys Ser
            260                 265                 270

Lys Asp Gly Asp Ile Phe Asn Pro Ala Cys Leu Pro Ile Tyr Gln Asp
        275                 280                 285

Met Thr Gln Pro Leu Asn His Tyr Phe Ile Cys Ser Ser His Asn Thr
    290                 295                 300

Tyr Leu Val Gly Asp Gln Leu Cys Gly Gln Ser Ser Val Glu Gly Tyr
305                 310                 315                 320

Ile Arg Ala Leu Lys Arg Gly Cys Arg Cys Val Glu Val Asp Val Trp
                325                 330                 335

Asp Gly Pro Ser Gly Glu Pro Val Val Tyr His Gly His Thr Leu Thr
            340                 345                 350

Ser Arg Ile Leu Phe Lys Asp Val Val Ala Thr Val Ala Gln Tyr Ala
        355                 360                 365

Phe Gln Thr Ser Asp Tyr Pro Val Ile Leu Ser Leu Glu Thr His Cys
    370                 375                 380

Ser Trp Glu Gln Gln Gln Thr Met Ala Arg His Leu Thr Glu Ile Leu
385                 390                 395                 400

Gly Glu Gln Leu Leu Ser Thr Thr Leu Asp Gly Val Leu Pro Thr Gln
                405                 410                 415

Leu Pro Ser Pro Glu Leu Arg Arg Lys Ile Leu Val Lys Gly Lys Lys
            420                 425                 430

Leu Thr Leu Glu Glu Asp Leu Glu Tyr Glu Glu Glu Ala Glu Pro
        435                 440                 445

Glu Leu Glu Glu Ser Glu Leu Ala Leu Glu Ser Gln Phe Glu Thr Glu
    450                 455                 460

Pro Glu Pro Gln Glu Gln Asn Leu Gln Asn Lys Asp Lys Lys Lys
465                 470                 475                 480

Ser Lys Pro Ile Leu Cys Pro Ala Leu Ser Ser Leu Val Ile Tyr Leu
                485                 490                 495

Lys Ser Val Ser Phe Arg Ser Phe Thr His Ser Lys Glu His Tyr His
            500                 505                 510

Phe Tyr Glu Ile Ser Ser Phe Ser Glu Thr Lys Ala Lys Arg Leu Ile
        515                 520                 525

Lys Glu Ala Gly Asn Glu Phe Val Gln His Asn Thr Trp Gln Leu Ser
    530                 535                 540

Arg Val Tyr Pro Ser Gly Leu Arg Thr Asp Ser Ser Asn Tyr Tyr Asn
545                 550                 555                 560
```

-continued

```
Pro Gln Glu Leu Trp Asn Ala Gly Cys Gln Met Val Ala Met Asn Met
                565                 570                 575
Gln Thr Ala Gly Leu Glu Met Asp Ile Cys Asp Gly His Phe Arg Gln
            580                 585                 590
Asn Gly Gly Cys Gly Tyr Val Leu Lys Pro Asp Phe Leu Arg Asp Ile
        595                 600                 605
Gln Ser Ser Phe His Pro Glu Lys Pro Ile Ser Pro Phe Lys Ala Gln
    610                 615                 620
Thr Leu Leu Asn Gln Val Ile Ser Val Gln Gln Leu Pro Lys Val Asp
625                 630                 635                 640
Lys Thr Lys Glu Gly Ser Ile Val Asp Pro Leu Val Lys Val Gln Ile
                645                 650                 655
Phe Gly Val Arg Leu Asp Thr Ala Arg Gln Glu Thr Asn Tyr Val Glu
            660                 665                 670
Asn Asn Gly Phe Asn Pro Tyr Trp Gly Gln Thr Leu Cys Phe Arg Val
        675                 680                 685
Leu Val Pro Glu Leu Ala Met Leu Arg Phe Val Val Met Asp Tyr Asp
    690                 695                 700
Trp Lys Ser Arg Asn Asp Phe Ile Gly Gln Tyr Thr Leu Pro Trp Thr
705                 710                 715                 720
Cys Met Gln Gln Gly Tyr Arg His Ile His Leu Leu Ser Lys Asp Gly
                725                 730                 735
Ile Ser Leu Arg Pro Ala Ser Ile Phe Val Tyr Ile Cys Ile Gln Glu
            740                 745                 750
Gly Leu Glu Gly Asp Glu Ser
        755

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Primer 1

<400> SEQUENCE: 7
gtgatggcgt ccctgctgca agaccag                                        27

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Primer 2

<400> SEQUENCE: 8
cctcaggact catcccctc caggcc                                          26

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Primer 3

<400> SEQUENCE: 9
cacacattca aaggagcact accac                                          25

<210> SEQ ID NO 10
<211> LENGTH: 21
<212> TYPE: DNA
```

```
<213> ORGANISM: Artificial Sequence
<220> FEATURE:
<223> OTHER INFORMATION: Description of Artificial Sequence: Primer 4

<400> SEQUENCE: 10
ctcatccccc tccaggcctt c                                              21

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Primer 5

<400> SEQUENCE: 11
ggtcttactc cttggaggcc atgt                                           24

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Primer 6

<400> SEQUENCE: 12
ccatcctaat acgactcact atagggc                                        27
```

HUMAN PHOSPHOLIPASE C DELTA 5

FIELD OF THE INVENTION

Figure 1:
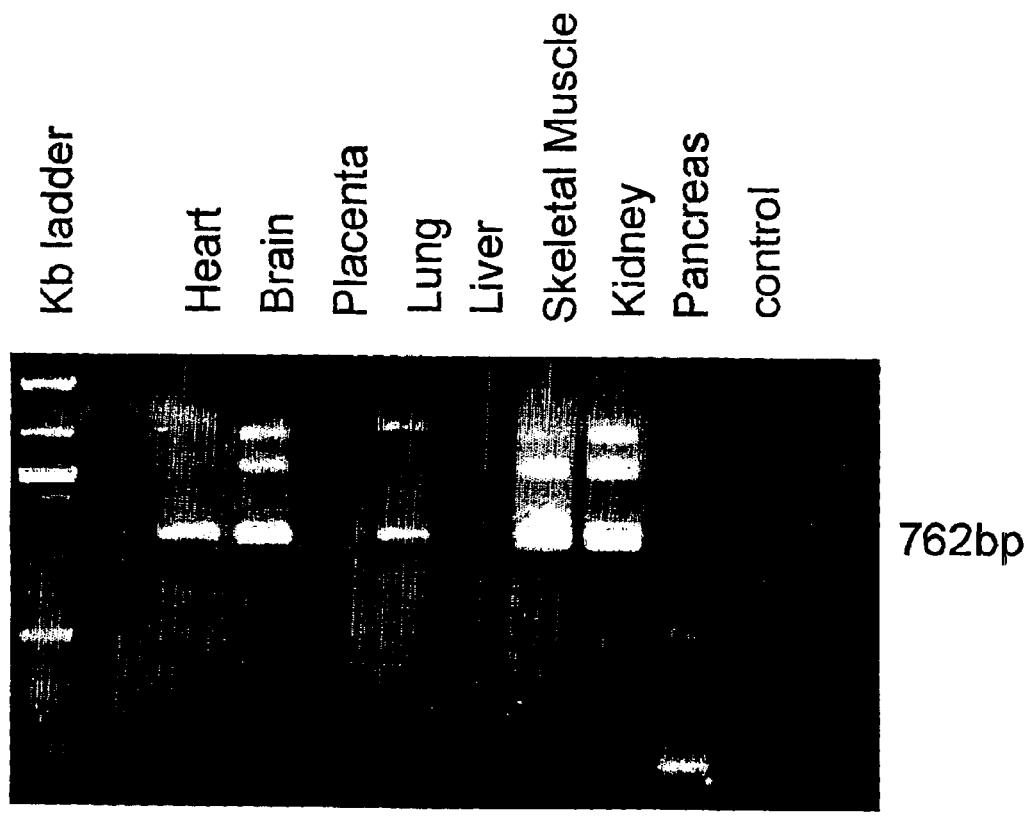

This invention relates to newly identified polypeptides and polynucleotides encoding such polypeptides sometimes hereinafter refered to as "phospholipase C delta 5 (PLCD5)", to their use in diagnosis and in identifying compounds that may be agonists, antagonists that are potentially useful in therapy, and to production of such polypeptides and polynucleotides.

BACKGROUND OF THE INVENTION

The drug discovery process is currently undergoing a fundamental revolution as it embraces "functional genomics", that is, high throughput genome- or gene-based biology. This approach as a means to identify genes and gene products as therapeutic targets is rapidly superceding earlier approaches based on "positional cloning". A phenotype, that is a biological function or genetic disease, would be identified and this would then be tracked back to the responsible gene, based on its genetic map position.

Functional genomics relies heavily on high-throughput DNA sequencing technologies and the various tools of bioinformatics to identify gene sequences of potential interest from the many molecular biology databases now available. There is a continuing need to identify and characterise further genes and their related polypeptides/proteins, as targets for drug discovery.

Diseases to be treated including but are not limited to deep vein thrombosis, instable angina pectoris, PTCA (percutane transluminal coronary angiography), thrombo embolic insult, dissiminated intravascular coagulation, arteriosclerosis, epilepsy, depression, neurodegenerative diseases, stroke, seizure, rheumatoid arthritis and immune disorders.

SUMMARY OF THE INVENTION

The present invention relates to phospholipase C delta 5 (PLCD5), in particular phospholipase C delta 5 (PLCD5) polypeptides, phospholipase C delta 5 (PLCD5) polynucleotides and splice variants thereof, recombinant materials and methods for their production. Such polypeptides and polynucleotides are of interest in relation to methods of treatment of certain diseases, including, but not limited to, see background of invention, hereinafter referred to as "diseases of the invention". In a further aspect, the invention relates to methods for identifying agonists and antagonists (e.g., inhibitors) using the materials provided by the invention, and treating conditions associated with phospholipase C delta 5 (PLCD5); imbalance with the identified compounds. In a still further aspect, the invention relates to diagnostic assays for detecting diseases associated with inappropriate phospholipase C delta 5(PLCD5) activity or levels.

DESCRIPTION OF THE INVENTION

In a first aspect, the present invention relates to phospholipase C delta 5 (PLCD5) polypeptides. Such polypeptides include:

(a) a polypeptide encoded by a polynucleotide comprising the sequence of SEQ ID NO: 1 or SEQ ID NO: 3 or SEQ ID NO: 5;

(b) apolypeptide comprising a polypeptide sequence having at least 95%, 96%, 97%, 98%, or 99% identity to the polypeptide sequences of SEQ ID NO: 2 or SEQ ID NO: 4 or SEQ ID NO: 6;

(c) a polypeptide comprising the polypeptide sequence of SEQ ID NO: 2 or SEQ ID NO: 4 or SEQ ID NO: 6;

(d) a polypeptide having at least 95%, 96%, 97%, 98%, or 99% identity to the polypeptide sequences of SEQ ID NO: 2 or SEQ ID NO: 4 or SEQ ID NO: 6;

(e) the polypeptide sequence of SEQ ID NO: 2 or SEQ ID NO: 4 or SEQ ID NO: 6; and (f) a polypeptide having or comprising a polypeptide sequence that has an Identity Index of 0.95, 0.96, 0.97, 0.98, or 0.99 compared to the polypeptide sequence of SEQ ID NO: 2 or SEQ ID NO: 4 or SEQ ID NO: 6;

(g) fragments and variants of such polypeptides in (a) to (f.

Polypeptides of the present invention are believed to be members of the phosphatidylinositol-specific phospholipase C (PLC) family of polypeptides. They are therefore of interest because phospholipase C hydrolyses phosphatidylinositol 4,5-bisphosphate (PIP2) and the products are inositol 1,4,5-trisphosphate (IP3), which releases calcium from the sarcoplasmatic reticulum and 1,2-diacylglycerol, which activates protein kinase C.

The biological properties of the phospholipase C delta 5 (PLCD5) are hereinafter referred to as "biological activity of phospholipase C delta 5(PLCD5)" or "phospholipase C delta 5 (PLCD5) activity". Preferably, a polypeptide of the present invention exhibits at least one biological activity of phospholipase C delta 5 (PLCD5).

Polypeptides of the present invention also includes variants of the aforementioned polypeptides, including all allelic forms and splice variants. Such polypeptides vary from the reference polypeptide by insertions, deletions, and substitutions that may be conservative or non-conservative, or any combination thereof. Particularly preferred variants are those in which several, for instance from 50 to 30, from 30 to 20, from 20 to 10, from 10 to 5, from 5 to 3, from 3 to 2, from 2 to 1 or 1 amino acids are inserted, substituted, or deleted, in any combination.

Preferred fragments of polypeptides of the present invention include a polypeptide comprising an amino acid sequence having at least 30, 50 or 100 contiguous amino acids from the amino acid sequence of SEQ ID NO: 2 or SEQ ID NO: 4 or SEQ ID NO:6, or a polypeptide comprising an amino acid sequence having at least 30, 50 or 100 contiguous amino acids truncated or deleted from the amino acid sequence of SEQ ID NO: 2 or SEQ ID NO: 4 or SEQ ID NO: 6. Preferred fragments are biologically active fragments that mediate the biological activity of phospholipase C delta 5 (PLCD5), including those with a similar activity or an improved activity, or with a decreased undesirable activity. Also preferred are those fragments that are antigenic or immunogenic in an animal, especially in a human.

Fragments of the polypeptides of the invention may be employed for producing the corresponding full-length polypeptide by peptide synthesis; therefore, these variants may be employed as intermediates for producing the full-length polypeptides of the invention. The polypeptides of the present invention may be in the form of the "mature" protein or may be a part of a larger protein such as a precursor or a fusion protein. It is often advantageous to include an additional amino acid sequence that contains secretory or leader sequences, pro-sequences, sequences that aid in purification, for instance multiple histidine residues, or an additional sequence for stability during recombinant production.

Polypeptides of the present invention can be prepared in any suitable manner, for instance by isolation form naturally occuring sources, from genetically engineered host cells comprising expression systems (vide infra) or by chemical synthesis, using for instance automated peptide synthesisers, or a combination of such methods. Means for preparing such polypeptides are well understood in the art.

In a further aspect, the present invention relates to phospholipase C delta 5 (PLCD5) polynucleotides. Such polynucleotides include:

(a) a polynucleotide comprising a polynucleotide sequence having at least 95%, 96%, 97%, 98%, or 99% identity to the polynucleotide squences of SEQ ID NO: 1 or SEQ ID NO: 3 or SEQ ID NO: 5;

(b) a polynucleotide comprising the polynucleotides of SEQ ID NO: 1 or SEQ ID NO: 3 or SEQ ID NO: 5;

(c) a polynucleotide having at least 95%, 96%, 97%, 98%, or 99% identity to the polynucleotides of SEQ ID NO: 1 or SEQ ID NO: 3 or SEQ ID NO: 5;

(d) the polynucleotides of SEQ ID NO: 1 or SEQ ID NO: 3 or SEQ ID NO: 5;

(e) a polynucleotide comprising a polynucleotide sequence encoding a polypeptide sequence having at least 95%, 96%, 97%, 98%, or 99% identity to the polypeptide sequences of SEQ ID NO: 2 or SEQ ID NO: 4 or SEQ ID NO: 6;

(f) a polynucleotide comprising a polynucleotide sequence encoding the polypeptides of SEQ ID NO: 2 or SEQ ID NO: 4 or SEQ ID NO: 6;

(g) a polynucleotide having a polynucleotide sequence encoding a polypeptide sequence having at least 95%, 96%, 97%, 98%, or 99% identity to the polypeptide sequences of SEQ ID NO: 2 or SEQ ID NO: 4 or SEQ ID NO: 6;

(h) a polynucleotide encoding the polypeptide of SEQ ID NO: 2 or SEQ ID NO: 4 or SEQ ID NO: 6;

(i) a polynucleotide having or comprising a polynucleotide sequence that has an Identity Index of 0.95, 0.96, 0.97, 0.98, or 0.99 compared to the polynucleotide sequences of SEQ ID NO: 1 or SEQ ID NO: 3 or SEQ ID NO: 5;

(j) a polynucleotide having or comprising a polynucleotide sequence encoding a polypeptide sequence that has an Identity Index of 0.95, 0.96, 0.97, 0.98, or 0.99 compared to the polypeptide sequences of SEQ ID NO: 2 or SEQ ID NO: 4 or SEQ ID NO: 6; and polynucleotides that are fragments and variants of the above mentioned polynucleotides or that are complementary to above mentioned polynucleotides, over the entire length thereof.

Preferred fragments of polynucleotides of the present invention include a polynucleotide comprising an nucleotide sequence having at least 15, 30, 50 or 100 contiguous nucleotides from the sequences of SEQ ID NO: 1 or SEQ ID NO: 3 or SEQ ID NO:5, or a polynucleotide comprising an sequence having at least 30, 50 or 100 contiguous nucleotides truncated or deleted from the sequence of SEQ ID NO: 1 or SEQ ID NO: 3 or SEQ ID NO: 5.

Preferred variants of polynucleotides of the present invention include splice variants, allelic variants, and polymorphisms, including polynucleotides having one or more single nucleotide polymorphisms (SNPs).

Polynucleotides of the present invention also include polynucleotides encoding polypeptide variants that comprise the amino acid sequence of SEQ ID NO: 2 or SEQ ID NO: 4 or SEQ ID NO: 6 and in which several, for instance from 50 to 30, from 30 to 20, from 20 to 10, from 10 to 5, from 5 to 3, from 3 to 2, from 2 to 1 or 1 amino acid residues are substituted, deleted or added, in any combination.

In a further aspect, the present invention provides polynucleotides that are RNA transcripts of the DNA sequences of the present invention. Accordingly, there is provided an RNA polynucleotide that:

(a) comprises an RNA transcript of the DNA sequence encoding the polypeptides of SEQ ID NO: 2 or SEQ ID NO: 4 or SEQ ID NO: 6;

(b) is the RNA transcript of the DNA sequence encoding the polypeptides of SEQ ID NO: 2 or SEQ ID NO: 4 or SEQ ID NO: 6;

(c) comprises an RNA transcript of the DNA sequences of SEQ ID NO: 1 or SEQ ID NO: 3 or SEQ ID NO: 5; or (d) is the RNA transcript of the DNA sequence of SEQ ID NO: 1 or SEQ ID NO: 3 or SEQ ID NO: 5;

and RNA polynucleotides that are complementary thereto.

The polynucleotide sequences of SEQ ID NO: 1 or SEQ ID NO: 3 or SEQ ID NO: 5 shows homology with *R. norvegicus* phospholipase C delta 4 (PRF: 2206431A). Rhee S G and Lee S B (1996) J Biol Chem, 271(1), 25–31. The polynucleotide sequence of SEQ ID NO: 1 or SEQ ID NO: 3 or SEQ ID NO: 5 is a cDNA sequence that encodes the polypeptide of SEQ ID NO: 2. and SEQ ID NO: 4 or SEQ ID NO: 6 The polynucleotide sequence encoding the polypeptide of SEQ ID NO: 2 or SEQ ID NO: 4 or SEQ ID NO: 6 may be identical to the polypeptide encoding sequence of SEQ ID NO: 1 and SEQ ID NO: 4 or SEQ ID NO: 6, or it may be a sequence other than SEQ ID NO: 1 and SEQ ID NO: 3 or SEQ ID NO: 5, which, as a result of the redundancy (degeneracy) of the genetic code, also encodes the polypeptides of SEQ ID NO: 2 or SEQ ID NO: 4 or SEQ ID NO: 6. The polypeptide of the SEQ ID NO: 2 and SEQ ID NO: 4 or SEQ ID NO: 6 are related to other proteins of the phosphatidylinositol-specific phospholipase C (PLC) family, having homology and/or structural similarity with *R. norvegicus* phospholipase C delta 4 (PRF: 2206431A). Rhee S G and Lee S B (1996) J Biol Chem, 271(1), 25–31.

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one phospholipase C delta 5 (PLCD5) activity.

Polynucleotides of the present invention may be obtained using standard cloning and screening techniques from a cDNA library derived from mRNA in cells of human heart, (see for instance, Sambrook et al., Molecular Cloning: A Laboratory Manual, 2nd Ed., Cold Spring Harbor Laboratory Press, Cold Spring Harbor, N.Y. (1989)). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself, or the coding sequence for the mature polypeptide in reading frame with other coding sequences, such as those encoding a leader or secretory sequence, a pre-, or pro- or prepro-protein sequence, or other fusion peptide portions. For example, a marker sequence that facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Polynucleotides that are identical, or have sufficient identity to a polynucleotide sequence of SEQ ID NO: 1 or SEQ ID NO: 3 or SEQ ID NO: 5, may be used as hybridization probes for cDNA and genomic DNA or as primers for a nucleic acid amplification reaction (for instance, PCR). Such probes and primers may be used to isolate full-length cDNAs and genomic clones encoding polypeptides of the present invention and to isolate cDNA and genomic clones of other genes (including genes encoding paralogs from human sources and orthologs and paralogs from species other than human) that have a high sequence similarity to SEQ ID NO: 1 or SEQ ID NO: 3 or SEQ ID NO: 5, typically at least 95% identity. Preferred probes and primers will generally comprise at least 15 nucleotides, preferably, at least 30 nucleotides and may have at least 50, if not at least 100 nucleotides. Particularly preferred probes will have between 30 and 50 nucleotides: Particularly preferred primers will have between 20 and 25 nucleotides.

A polynucleotide encoding a polypeptide of the present invention, including homologs from species other than human, may be obtained by a process comprising the steps of screening a library under stringent hybridization conditions with a labeled probe having the sequence of SEQ ID NO: 1 or SEQ ID NO: 3 or SEQ ID NO: 5, or a fragment thereof, preferably of at least 15 nucleotides; and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA; followed by washing the filters in 0.1×SSC at about 65° C. Thus the present invention also includes polynucleotides, preferably with a nucleotide sequence of at least 100, obtained by screening a library under stringent hybridization conditions with a labeled probe having the sequence of SEQ ID NO: 1 or SEQ ID NO: 3 or SEQ ID NO: 5 or a fragment thereof, preferably of at least 15 nucleotides.

The skilled artisan will appreciate that, in many cases, an isolated cDNA sequence will be incomplete, in that the region coding for the polypeptide does not extend all the way through to the 5' terminus. This is a consequence of reverse transcriptase, an enzyme with inherently low "processivity" (a measure of the ability of the enzyme to remain attached to the template during the polymerisation reaction), failing to complete a DNA copy of the mRNA template during first strand cDNA synthesis.

There are several methods available and well known to those skilled in the art to obtain full-length cDNAs, or extend short cDNAs, for example those based on the method of Rapid Amplification of cDNA ends (RACE) (see, for example, Frohman et al., Proc Nat Acad Sci USA 85, 8998–9002, 1988). Recent modifications of the technique, exemplified by the Marathon (trade mark) technology (Clontech Laboratories Inc.) for example, have significantly simplified the search for longer cDNAs. In the Marathon (trade mark) technology, cDNAs have been prepared from mRNA extracted from a chosen tissue and an 'adaptor' sequence ligated onto each end. Nucleic acid amplification (PCR) is then carried out to amplify the "missing" 5' end of the cDNA using a combination of gene specific and adaptor specific oligonucleotide primers. The PCR reaction is then repeated using 'nested' primers, that is, primers designed to anneal within the amplified product (typically an adaptor specific primer that anneals further 3' in the adaptor sequence and a gene specific primer that anneals further 5' in the known gene sequence). The products of this reaction can then be analysed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression systems. Accordingly, in a further aspect, the present invention relates to expression systems comprising a polynucleotide or polynucleotides of the present invention, to host cells which are genetically engineered with such expression systems and to the production of polypeptides of the invention by recombinant techniques.

Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Polynucleotides may be introduced into host cells by methods described in many standard laboratory manuals, such as Davis et al., Basic Methods in Molecular Biology (1986) and Sambrook et al.(ibid). Preferred methods of introducing polynucleotides into host cells include, for instance, calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as *Streptococci, Staphylococci, E. coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector that is able to maintain, propagate or express a polynucleotide to produce a polypeptide in a host may be used. The appropriate polynucleotide sequence may be inserted into an expression system by any of a variety of well-known and routine techniques, such as, for example, those set forth in Sambrook et al., (ibid). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

If a polypeptide of the present invention is to be expressed for use in screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cells must first be lysed before the polypeptide is recovered.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during intracellular synthesis, isolation and/or purification.

Polynucleotides of the present invention may be used as diagnostic reagents, through detecting mutations in the associated gene. Detection of a mutated form of the gene characterised by the polynucleotide of SEQ ID NO: 1 or SEQ ID NO: 3 or SEQ ID NO: 5 in the cDNA or genomic sequence and which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques well known in the art.

Nucleic acids for diagnosis may be obtained from a subject's cells, such as from blood, urine, saliva, tissue biopsy or autopsy material. The genomic DNA may be used directly for detection or it may be amplified enzymatically by using PCR, preferably RT-PCR, or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled phospholipase C delta 5 (PLCD5) nucleotide sequences. Perfectly matched sequences can be distinguished from mismatched duplexes by RNase digestion or by differences in melting temperatures. DNA sequence difference may also be detected by alterations in the electrophoretic mobility of DNA fragments in gels, with or without denaturing agents, or by direct DNA sequencing (see, for instance, Myers et al., Science (1985) 230:1242). Sequence changes at specific locations may also be revealed by nuclease protection assays, such as RNase and S1 protection or the chemical cleavage method (see Cotton et al., Proc Natl Acad Sci USA (1985) 85: 4397–4401).

An array of oligonucleotides probes comprising phospholipase C delta 5 (PLCD5) polynucleotide sequence or fragments thereof can be constructed to conduct efficient screening of e.g., genetic mutations. Such arrays are preferably high density arrays or grids. Array technology methods are well known and have general applicability and can be used to address a variety of questions in molecular genetics including gene expression, genetic linkage, and genetic variability, see, for example, M. Chee et al., Science, 274, 610–613 (1996) and other references cited therein.

Detection of abnormally decreased or increased levels of polypeptide or mRNA expression may also be used for diagnosing or determining susceptibility of a subject to a disease of the invention. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods. Assay techniques that can be used to determine levels of a protein such as a polypeptide of the present invention, in a sample derived from a host are well-known to those of skill in the art. Such assay methods include radioimmunoassays, competitive-binding assays, Western Blot analysis and ELISA assays.

Thus in another aspect, the present invention relates to a diagonostic kit comprising:

(a) a polynucleotide of the present invention, preferably the nucleotide sequence of SEQ ID NO: 1 or SEQ ID NO: 4 or SEQ ID NO: 5, or a fragment or an RNA transcript thereof;

(b) a nucleotide sequence complementary to that of (a);

(c) a polypeptide of the present invention, preferably the polypeptide of SEQ ID NO: 2 or SEQ ID NO: 4 or SEQ ID NO: 6 or a fragment thereof; or (d) an antibody to a polypeptide of the present invention, preferably to the polypeptide of SEQ ID NO: 2 or SEQ ID NO: 4 or SEQ ID NO: 6.

It will be appreciated that in any such kit, (a), (b), (c) or (d) may comprise a substantial component. Such a kit will be of use in diagnosing a disease or susceptibility to a disease, particularly diseases of the invention, amongst others.

The polynucleotide sequences of the present invention are valuable for chromosome localisation studies. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (co-inheritance of physically adjacent genes). Precise human chromosomal localisations for a genomic sequence (gene fragment etc.) can be determined using Radiation Hybrid (RH) Mapping (Walter, M. Spillett, D., Thomas, P., Weissenbach, J., and. Goodfellow, P., (1994) A method for constructing radiation hybrid maps of whole genomes, Nature Genetics 7, 22–28). A number of RH panels are available from Research Genetics (Huntsville, Ala., USA) e.g. the GeneBridge4 RH panel (Hum Mol Genet Mar; 5, 1996(3):339–46 A radiation hybrid map of the human genome. Gyapay G, Schmitt K, Fizames C, Jones H, Vega-Czarny N, Spillett D, Muselet D, Prud'Homme J F, Dib C, Auffray C, Morissette J, Weissenbach J, Goodfellow P N). To determine the chromosomal location of a gene using this panel, 93 PCRs are performed using primers designed from the gene of interest on RH DNAs. Each of these DNAs contains random human genomic fragments maintained in a hamster background (human/hamster hybrid cell lines). These PCRs result in 93 scores indicating the presence or absence of the PCR product of the gene of interest. These scores are compared with scores created using PCR products from genomic sequences of known location. This comparison is conducted at http://www.genome.wi.mit.edu/. The gene of the present invention maps to human chromosome 2q34–2q35, Interval D2S164–D2S163.

The polynucleotide sequences of the present invention are also valuable tools for tissue expression studies. Such studies allow the determination of expression patterns of polynucleotides of the present invention which may give an indication as to the expression patterns of the encoded polypeptides in tissues, by detecting the mRNAs that encode them. The techniques used are well known in the art and include in situ hydridisation techniques to clones arrayed on a grid, such as cDNA microarray hybridisation (Schena et al, Science, 270, 467–470, 1995 and Shalon et al, Genome Res, 6, 639–645, 1996) and nucleotide amplification techniques such as PCR. A preferred method uses the TAQMAN (Trade mark) technology available from Perkin Elmer. Results from these studies can provide an indication of the normal function of the polypeptide in the organism. In addition, comparative studies of the normal expression pattern of mRNAs with that of mRNAs encoded by an alternative form of the same gene (for example, one having an alteration in polypeptide coding potential or a regulatory mutation) can provide valuable insights into the role of the polypeptides of the present invention, or that of inappropriate expression thereof in disease. Such inappropriate expression may be of a temporal, spatial or simply quantitative nature.

The polypeptides of the present invention are expressed in heart, brain, lung and retina.

A further aspect of the present invention relates to antibodies. The polypeptides of the invention or their fragments, or cells expressing them, can be used as immunogens to produce antibodies that are immunospecific for polypeptides of the present invention. The term "immunospecific" means that the antibodies have substantially greater affinity for the polypeptides of the invention than their affinity for other related polypeptides in the prior art.

Antibodies generated against polypeptides of the present invention may be obtained by administering the polypeptides or epitope-bearing fragments, or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., Nature (1975) 256:495–497), the trioma technique, the human B-cell hybridoma technique (Kozbor et al., Immunology Today (1983) 4:72) and the EBV-hybridoma technique (Cole et al., Monoclonal Antibodies and Cancer Therapy, 77–96, Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography. Antibodies against polypeptides of the present invention may also be employed to treat diseases of the invention, amongst others.

Polypeptides and polynucleotides of the present invention -may also be used as vaccines. Accordingly, in a further aspect, the present invention relates to a method for inducing an immunological response in a mammal that comprises inoculating the mammal with a polypeptide of the present invention, adequate to produce antibody and/or T cell immune response, including, for example, cytokine-producing T cells or cytotoxic T cells, to protect said animal from disease, whether that disease is already established within the individual or not. An immunological response in a mammal may also be induced by a method comprises delivering a polypeptide of the present invention via a vector directing expression of the polynucleotide and coding for the polypeptide in vivo in order to induce such an immunological response to produce antibody to protect said animal from diseases of the invention. One way of administering the vector is by accelerating it into the desired cells as a coating on particles or otherwise. Such nucleic acid vector may comprise DNA, RNA, a modified nucleic acid, or a DNA/RNA hybrid. For use a vaccine, a polypeptide or a nucleic acid vector will be normally provided as a vaccine formulation (composition). The formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions that may contain anti-oxidants, buffers, bacteriostats and solutes that render the formulation instonic with the blood of the recipient; and aqueous and non-aqueous sterile suspensions that may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Polypeptides of the present invention have one or more biological functions that are of relevance in one or more disease states, in particular the diseases of the invention hereinbefore mentioned. It is therefore useful to to identify compounds that stimulate or inhibit the function or level of the polypeptide. Accordingly, in a further aspect, the present invention provides for a method of screening compounds to identify those that stimulate or inhibit the function or level of the polypeptide. Such methods identify agonists or antagonists that may be employed for therapeutic and prophylactic purposes for such diseases of the invention as hereinbefore mentioned. Compounds may be identified from a variety of sources, for example, cells, cell-free preparations, chemical libraries, collections of chemical compounds, and natural product mixtures. Such agonists or antagonists so-identified may be natural or modified substrates, ligands, receptors, enzymes, etc., as the case may be, of the polypeptide; a structural or functional mimetic thereof (see Coligan et al., Current Protocols in Immunology 1(2):Chapter 5 (1991)) or a small molecule.

The screening method may simply measure the binding of a candidate compound to the polypeptide, or to cells or membranes bearing the polypeptide, or a fusion protein thereof, by means of a label directly or indirectly associated with the candidate compound. Alternatively, the screening method may involve measuring or detecting (qualitatively or quantitatively) the competitive binding of a candidate compound to the polypeptide against a labeled competitor (e.g. agonist or antagonist). Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Further, the screening methods may simply comprise the steps of mixing a candidate compound with a solution containing a polypeptide of the present invention, to form a mixture, measuring a phospholipase C delta 5 (PLCD5) activity in the mixture, and comparing the phospholipase C delta 5 (PLCD5) activity of the mixture to a control mixture which contains no candidate compound.

Polypeptides of the present invention may be employed in conventional low capacity screening methods and also in high-throughput screening (HTS) formats. Such HTS formats include not only the well-established use of 96- and, more recently, 384-well micotiter plates but also emerging methods such as the nanowell method described by Schullek et al, Anal Biochem., 246, 20–29, (1997).

Fusion proteins, such as those: made from Fc portion and phospholipase C delta 5 (PLCD5) polypeptide, as hereinbefore described, can also be used for high-throughput screening assays to identify antagonists for the polypeptide of the present invention (see D. Bennett et al., J Mol Recognition, 8:52–58 (1995); and K. Johanson et al., J Biol Chem, 270(16):9459–9471 (1995)).

Screening Techniques

The polynucleotides, polypeptides and antibodies to the polypeptide of the present invention may also be used to configure screening methods for detecting the effect of added compounds on the production of mRNA and polypeptide in cells. For example, an ELISA assay may be constructed for measuring secreted or cell associated levels of polypeptide using monoclonal and polyclonal antibodies by standard methods known in the art. This can be used to discover agents that may inhibit or enhance the production of polypeptide (also called antagonist or agonist, respectively) from suitably manipulated cells or tissues.

A polypeptide of the present invention may be used to identify membrane bound or soluble receptors, if any, through standard receptor binding techniques known in the art. These include, but are not limited to, ligand binding and crosslinking assays in which the polypeptide is labeled with a radioactive isotope (for instance, $^{125}$I), chemically modified (for instance, biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. These screening methods may also be used to identify agonists and antagonists of the polypeptide that compete with the binding of the polypeptide to its receptors, if any. Standard methods for conducting such assays are well understood in the art.

Examples of antagonists of polypeptides of the present invention include antibodies or, in some cases, oligonucleotides or proteins that are closely related to the ligands, substrates, receptors, enzymes, etc., as the case may be, of the polypeptide, e.g., a fragment of the ligands, substrates, receptors, enzymes, etc.; or a small molecule that bind to the polypeptide of the present invention but do not elicit a response, so that the activity of the polypeptide is prevented.

Screening methods may also involve the use of transgenic technology and phospholipase C delta 5 (PLCD5) gene. The art of constructing transgenic animals is well established. For example, the phospholipase C delta 5 (PLCD5) gene may be introduced through microinjection into the male pronucleus of fertilized oocytes, retroviral transfer into pre- or post-implantation embryos, or injection of genetically modified, such as by electroporation, embryonic stem cells into host blastocysts. Particularly useful transgenic animals are so-called "knock-in" animals in which an animal gene is replaced by the human equivalent within the genome of that animal. Knock-in transgenic animals are useful in the drug discovery process, for target validation, where the compound is specific for the human target. Other useful transgenic animals are so-called "knock-out" animals in which the expression of the animal ortholog of a polypeptide of the present invention and encoded by an endogenous DNA sequence in a cell is partially or completely annulled. The gene knock-out may be targeted to specific cells or tissues, may occur only in certain cells or tissues as a consequence of the limitations of the technology, or may occur in all, or substantially all, cells in the animal. Transgenic animal technology also offers a whole animal expression-cloning system in which introduced genes are expressed to give large amounts of polypeptides of the present invention Screening kits for use in the above described methods form a further aspect of the present invention. Such screening kits comprise:

(a) a polypeptide of the present invention;
(b) a recombinant cell expressing a polypeptide of the present invention;
(c) a cell membrane expressing a polypeptide of the present invention; or
(d) an antibody to a polypeptide of the present invention; which polypeptide is preferably that of SEQ ID NO: 2 or SEQ ID NO: 4 or SEQ ID NO: 6.

It will be appreciated that in any such kit, (a), (b), (c) or (d) may comprise a substantial component.

Glossary

The following definitions are provided to facilitate understanding of certain terms used frequently hereinbefore.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Polynucleotide" generally refers to any polyribonucleotide (RNA) or polydeoxribonucleotide (DNA), which may be unmodified or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any polypeptide comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques that are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, Proteins—Structure and Molecular Properties, 2nd Ed., T. E. Creighton, W. H. Freeman and Company, New York, 1993; Wold, F., Post-translational Protein Modifications: Perspectives and Prospects, 1–12, in Post-translational Covalent Modification of Proteins, B. C. Johnson, Ed., Academic Press, New York, 1983; Seifter et al., "Analysis for protein modifications and nonprotein cofactors", Meth Enzymol, 182, 626–646, 1990, and Rattan et al., "Protein Synthesis: Post-translational Modifications and Aging", Ann NY Acad Sci, 663, 48–62, 1992).

"Fragment" of a polypeptide sequence refers to a polypeptide sequence that is shorter than the reference sequence but that retains essentially the same biological function or activity as the reference polypeptide. "Fragment" of a polynucleotide sequence refers to a polynucleotide sequence that is shorter than the reference sequences of SEQ ID NO: 1 or SEQ ID NO: 3 or SEQ ID NO: 5.

"Variant" refers to a polynucleotide or polypeptide that differs from a reference polynucleotide or polypeptide, but retains the essential properties thereof. A typical variant of a polynucleotide differs in nucleotide sequence from the reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from the reference polypeptide. Generally, alterations are limited so that the sequences of the reference polypeptide and the variant are closely similar overall and, in many regions, identical. A variant and reference polypeptide may differ in amino acid sequence by one or more substitutions, insertions, deletions in any combination. A substituted or inserted amino acid residue may or may not be one encoded by the genetic code. Typical conservative substitutions include Gly, Ala; Val, Ile, Leu; Asp, Glu; Asn, Gln; Ser, Thr; Lys, Arg; and Phe and Tyr. A variant of a polynucleotide or polypeptide may be naturally occurring such as an allele, or it may be a variant that is not known to occur naturally. Non-naturally occurring variants of polynucleotides and polypeptides may be made by mutagenesis techniques or by direct synthesis. Also included as variants are polypeptides having one or more post-translational modifications, for instance glycosylation, phosphorylation, methylation, ADP ribosylation and the like. Embodiments include methylation of the N-terminal amino acid, phosphorylations of serines and threonines and modification of C-terminal glycines.

"Allele" refers to one of two or more alternative forms of a gene occuring at a given locus in the genome.

"Polymorphism" refers to a variation in nucleotide sequence (and encoded polypeptide sequence, if relevant) at a given position in the genome within a population.

"Single Nucleotide Polymorphism" (SNP) refers to the occurence of nucleotide variability at a single nucleotide position in the genome, within a population. An SNP may occur within a gene or within intergenic regions of the genome. SNPs can be assayed using Allele Specific Amplification (ASA). For the process at least 3 primers are required. A common primer is used in reverse complement to the polymorphism being assayed. This common primer can be between 50 and 1500 bps from the polymorphic base. The other two (or more) primers are identical to each other except that the final 3' base wobbles to match one of the two (or more) alleles that make up the polymorphism. Two (or more) PCR reactions are then conducted on sample DNA, each using the common primer and one of the Allele Specific Primers.

"Splice Variant" as used herein refers to cDNA molecules produced from RNA molecules initially transcribed from the same genomic DNA sequence but which have undergone alternative RNA splicing. Alternative RNA splicing occurs when a primary RNA transcript undergoes splicing, generally for the removal of introns, which results in the production of more than one mRNA molecule each of that may encode different amino acid sequences. The term splice variant also refers to the proteins encoded by the above cDNA molecules.

"Identity" reflects a relationship between two or more polypeptide sequences or two or more polynucleotide sequences, determined by comparing the sequences. In general, identity refers to an exact nucleotide to nucleotide or amino acid to amino acid correspondence of the two polynucleotide or two polypeptide sequences, respectively, over the length of the sequences being compared.

"% Identity"—For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

"Similarity" is a further, more sophisticated measure of the relationship between two polypeptide sequences. In general, "similarity" means a comparison between the amino acids of two polypeptide chains, on a residue by residue basis, taking into account not only exact correspondences between a between pairs of residues, one from each of the sequences being compared (as for identity) but also, where there is not an exact correspondence, whether, on an evolutionary basis, one residue is a likely substitute for the other. This likelihood has an associated "score" from which the "% similarity" of the two, sequences can then be determined.

Methods for comparing the identity and similarity of two or more sequences are well known in the art. Thus for instance, programs available in the Wisconsin Sequence Analysis Package, version 9.1 (Devereux J et al, Nucleic Acids Res, 12, 387–395, 1984, available from Genetics Computer Group, Madison, Wis., USA), for example the programs BESTFIT and GAP, may be used to determine the % identity between two polynucleotides and the % identity and the % similarity between two polypeptide sequences. BESTFIT uses the "local homology" algorithm of Smith and Waterman (J Mol Biol, 147,195–197, 1981, Advances in Applied Mathematics, 2, 482–489, 1981) and finds the best single region of similarity between two sequences. BEST-FIT is more suited to comparing two polynucleotide or two polypeptide sequences that are dissimilar in length, the program assuming that the shorter sequence represents a portion of the longer. In comparison, GAP aligns two sequences, finding a "maximum similarity", according to the algorithm of Neddleman and Wunsch (J Mol Biol, 48, 443–453, 1970). GAP is more suited to comparing sequences that are approximately the same length and an alignment is expected over the entire length. Preferably, the parameters "Gap Weight" and "Length Weight" used in each program are 50 and 3, for polynucleotide sequences and 12 and 4 for polypeptide sequences, respectively. Preferably, % identities and similarities are determined when the two sequences being compared are optimally aligned.

Other programs for determining identity and/or similarity between sequences are also known in the art, for instance the BLAST family of programs (Altschul S F et al, J Mol Biol, 215, 403–410,1990, Altschul S F et al, Nucleic Acids Res., 25:389–3402, 1997, available from the National Center for Biotechnology Information (NCBI), Bethesda, Md., USA and accessible through the home page of the NCBI at www.ncbi.nlm.nih.gov) and FASTA (Pearson W R, Methods in Enzymology, 183, 63–99, 1990; Pearson W R and Lipman D J, Proc Nat Acad Sci USA, 85, 2444–2448,1988, available as part of the Wisconsin Sequence Analysis Package).

Preferably, the BLOSUM62 amino acid substitution matrix (Henikoff S and Henikoff J G, Proc. Nat. Acad Sci. USA, 89, 10915–10919, 1992) is used in polypeptide sequence comparisons including where nucleotide sequences are first translated into amino acid sequences before comparison.

Preferably, the program BESTFIT is used to determine the % identity of a query polynucleotide or a polypeptide sequence with respect to a reference polynucleotide or a polypeptide sequence, the query and the reference sequence being optimally aligned and the parameters of the program set at the default value, as hereinbefore described.

"Identity Index" is a measure of sequence relatedness which may be used to compare a candidate sequence (polynucleotide or polypeptide) and a reference sequence. Thus, for instance, a candidate polynucleotide sequence having, for example, an Identity Index of 0.95 compared to a reference polynucleotide sequence is identical to the reference sequence except that the candidate polynucleotide sequence may include on average up to five differences per each 100 nucleotides of the reference sequence. Such differences are selected from the group consisting of at least one nucleotide deletion, substitution, including transition and transversion, or insertion. These differences may occur at the 5' or 3' terminal positions of the reference polynucleotide sequence or anywhere between these terminal positions, interspersed either individually among the nucleotides in the reference sequence or in one or more contiguous groups within the reference sequence. In other words, to obtain a polynucleotide sequence having an Identity Index of 0.95 compared to a reference polynucleotide sequence, an average of up to 5 in every 100 of the nucleotides of the in the reference sequence may be deleted, substituted or inserted, or any combination thereof, as hereinbefore described. The same applies mutatis mutandis for other values of the Identity Index, for instance 0.96, 0.97, 0.98 and 0.99.

Similarly, for a polypeptide, a candidate polypeptide sequence having, for example, an Identity Index of 0.95 compared to a reference polypeptide sequence is identical to the reference sequence except that the polypeptide sequence may include an average of up to five differences per each 100 amino acids of the reference sequence. Such differences are selected from the group consisting of at least one amino acid deletion, substitution, including conservative and non-conservative substitution, or insertion. These differences may occur at the amino- or carboxy-terminal positions of the reference polypeptide sequence or anywhere between these terminal positions, interspersed either individually among the amino acids in the reference sequence or in one or more contiguous groups within the reference sequence. In other words, to obtain a polypeptide sequence having an Identity Index of 0.95 compared to a reference polypeptide sequence, an average of up to 5 in every 100 of the amino acids in the reference sequence may be deleted, substituted or inserted, or any combination thereof, as hereinbefore described. The same applies mutatis mutandis for other values of the Identity Index, for instance 0.96, 0.97, 0.98 and 0.99.

The relationship between the number of nucleotide or amino acid differences and the Identity Index may be expressed in the following equation:

$$n_a \leq x_a - (x_a \cdot I),$$

in which:
$n_a$ is the number of nucleotide or amino acid differences,
$x_a$ is the total number of nucleotides or amino acids in SEQ ID NO:1, 2, 3, or SEQ ID NO:4, respectively,
I is the Identity Index,
· is the symbol for the multiplication operator, and
in which any non-integer product of $x_a$ and I is rounded down to the nearest integer prior to subtracting it from $x_a$.

"Homolog" is a generic term used in the art to indicate a polynucleotide or polypeptide sequence possessing a high degree of sequence relatedness to a reference sequence.

Such relatedness may be quantified by determining the degree of identity and/or similarity between the two sequences as hereinbefore defined. Falling within this generic term are the terms "ortholog", and "paralog". "Ortholog" refers to a polynucleotide or polypeptide that is the functional equivalent of the polynucleotide or polypeptide in another species. "Paralog" refers to a polynucleotideor polypeptide that within the same species which is functionally similar.

"Fusion protein" refers to a protein encoded by two, unrelated, fused genes or fragments thereof. Examples have been disclosed in U.S. Pat. Nos. 5,541,087, 5,726,044. In the case of Fc-PLCD5, employing an immunoglobulin Fc region as a part of a fusion protein is advantageous for performing the functional expression of Fc-PLCD5 or fragments of PLCD5, to improve pharmacokinetic properties of such a fusion protein when used for therapy and to generate a dimeric PLCD5. The Fc-PLCD5 DNA construct comprises in 5' to 3' direction, a secretion cassette, i.e. a signal sequence that triggers export from a mammalian cell, DNA encoding an immunoglobulin Fc region fragment, as a fusion partner, and a DNA, encoding PLCD5 or fragments thereof. In some uses it would be desirable to be able to alter the intrinsic functional properties (complement binding, Fc-Receptor binding) by mutating the functional Fc sides while leaving the rest of the fusion protein untouched or delete the Fc part completely after expression.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

Further Examples

Cloning of the Full Length Gene:

A marathon human skeletal muscle cDNA (Lot No.: 8110450) from clontech Laboratories GmbH, Heidelberg Germany was subjected to PCR using gene-specific primer No. 1 (SEQ ID NO: 7) and No. 2 (SEQ ID NO: 8) in reverse orientation. The conditions for PCR were 1,30 min at 94° C., 30 sec at 94° C. and 1 min 68° C. for 5 cycles, 30 sec at 94° C. and 1 min 66° C. for 5 cycles, 30 sec at 94° C. and 1 min 64° C. for 32 cycles followed by an extension step 3 min at 72° using the advantage polymerase (clontech). The cDNA amplification product was cloned and sequenced.

Tissue Distribution:

A set of normalised human cDNA was used to amplify a short gene fragment to examine the tissue distribution of PLCD5 For this purpose the clontech Multiple Tissue cDNA Panel I (clontech Laboratories GmbH, Heidelberg Germany) was used with two PLCD5 gene-specific primers No. 3 (SEQ ID NO: 9) and No. 3 (SEQ ID NO: 10) in reverse orientation. Using the advantage polymerase mixture purchased from clontech a 762 bp long PCR fragment could be amplified as indicated in the gel photo. The PCR conditions were 30 sec at 94° C. followed by 30 sec at 94° C., 1 min at 61° C. and 3 min at 68° C. for 30 cycles using the advantage polymerase (clontech). A G3PDH specific primer 5 (SEQ ID NO: 11) combined with primer 5 (SEQ ID NO: 12) served as the positive control and resulted in a 1,09 kb PCR product. The negative control PCR included sterile water as PCR template and gave no PCR product.

Figure Legend

FIG. 1: 1.1% agarose gel of multiple tissue cDNA panels. Human tissues, and controls are indicated. 20 µl of each PCR reaction were loaded on the gel.

What is claimed is:

1. An isolated polypeptide having phospholipase C delta 5 activity, selected from a group consisting of:
   (a) a polypeptide encoded by a polynucleotide comprising the sequence of SEQ ID NO: 3;
   (b) a polypeptide comprising a polypeptide sequence having at least 95% identity to the polypeptide sequence of SEQ ID NO: 4;
   (c) a polypeptide consisting of a polypeptide sequence having at least 95% identity to the polypeptide sequence of SEQ ID NO: 4;
   (d) a polypeptide sequence of SEQ ID NO: 4; and
   (e) a fragment of the polypeptides in (a) to (d), having phospholipase C delta 5 activity.

2. The polypeptide as claimed in claim 1, comprising the polypeptide sequence of SEQ ID NO: 4.

3. The polypeptide as claimed in claim 1, which is the polypeptide sequence of SEQ ID NO: 4.

4. A fusion protein comprising immunoglobulin Fc-region, and the polypeptide of claim 1.

* * * * *